(12) United States Patent
Vamvakas et al.

(10) Patent No.: US 10,182,992 B2
(45) Date of Patent: Jan. 22, 2019

(54) ABUSE-DETERRENT CONTROLLED RELEASE FORMULATIONS

(71) Applicant: PATHEON SOFTGELS INC., High Point, NC (US)

(72) Inventors: George Vamvakas, Greensboro, NC (US); Aqeel A Fatmi, High Point, NC (US)

(73) Assignee: Patheon Softgels Inc., High Point, NC (US)

( * ) Notice: Subject to any disclaimer, the term of this patent is extended or adjusted under 35 U.S.C. 154(b) by 150 days.

(21) Appl. No.: 14/679,062

(22) Filed: Apr. 6, 2015

(65) Prior Publication Data

US 2015/0283087 A1 Oct. 8, 2015

Related U.S. Application Data

(60) Provisional application No. 61/976,237, filed on Apr. 7, 2014, provisional application No. 62/101,431, filed on Jan. 9, 2015.

(51) Int. Cl.
*A61K 9/48* (2006.01)
*A61K 31/137* (2006.01)
*A61K 31/485* (2006.01)

(52) U.S. Cl.
CPC ............ *A61K 9/4866* (2013.01); *A61K 9/485* (2013.01); *A61K 9/4858* (2013.01); *A61K 9/4875* (2013.01); *A61K 31/137* (2013.01); *A61K 31/485* (2013.01)

(58) Field of Classification Search
CPC .............. A61K 2300/00; A61K 31/137; A61K 31/135; A61K 9/2866; A61K 9/2886; A61K 9/2846; A61K 9/0004; A61K 9/2027; A61K 9/28; A61K 31/4985; A61K 45/06; A61K 31/138; A61K 31/495; A61K 31/724; A61K 31/485; A61K 9/485; A61K 9/4858; A61K 9/4866; A61K 9/4875

See application file for complete search history.

(56) References Cited

U.S. PATENT DOCUMENTS

| 5,146,730 | A | 9/1992 | Sadek et al. |
| 5,459,983 | A | 10/1995 | Sadek et al. |
| 6,482,516 | B1 | 11/2002 | Sadek et al. |
| 8,685,445 | B2 | 4/2014 | Hassan et al. |
| 2004/0052731 | A1 | 3/2004 | Hirsh et al. |
| 2006/0115527 | A1 | 6/2006 | Hassan et al. |
| 2006/0165778 | A1 | 7/2006 | Hassan et al. |
| 2007/0092560 | A1 | 4/2007 | Sukuru |
| 2009/0082466 | A1* | 3/2009 | Babul ............... A61K 9/4858 514/646 |
| 2009/0232887 | A1* | 9/2009 | Odidi ................ A61K 9/06 424/457 |

OTHER PUBLICATIONS

International Search Report for PCT/2015/024422, dated Aug. 27, 2015.

* cited by examiner

*Primary Examiner* — Snigdha Maewall
(74) *Attorney, Agent, or Firm* — Brinks Gilson & Lione

(57) ABSTRACT

Described herein are abuse deterrent controlled release oral pharmaceutical compositions comprising and methods for making the same. In particular, an abuse deterrent controlled release oral pharmaceutical composition comprising a soft capsule and an abuse deterrent controlled release matrix comprising an active pharmaceutical ingredient are described.

4 Claims, 9 Drawing Sheets

FIGURE 1

| Physical manipulations performed at ambient conditions (ca. 25 °C) ||||
|---|---|---|---|
| Tampering Method ||||
| Crushing | Grating | Grinding | Cutting |
| 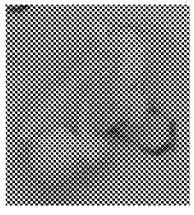 |  |  | 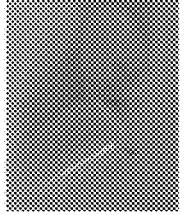 |
| The capsule was crushed but the material released was thick, waxy, sticky material that cannot be easily snorted, dispersed, dissolved, or extracted for injection. | The capsule was grated with a cheese grater. It released a thick, waxy, sticky material that cannot be easily snorted, dispersed, dissolved, or extracted for injection. | The capsule could not be ground in a coffee grinder. | A razor was used to cut the capsule. The thick, waxy, sticky fill material cannot be easily snorted, dispersed, dissolved, or extracted for injection. |

FIGURE 2

| Physical manipulations performed after storage at 40 °C for 2 hours | | | |
|---|---|---|---|
| Method of Tampering | | | |
| Crushing | Grating | Grinding | Cutting |
| 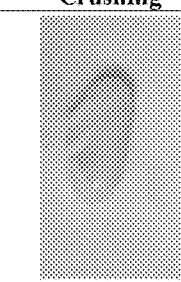 | 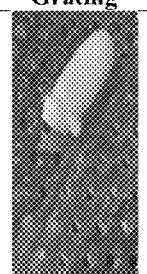 | 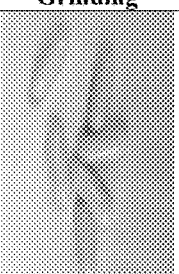 | 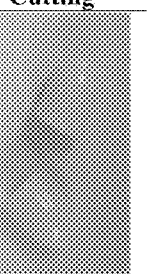 |
| The capsule behaved in the same manner as under ambient conditions. | The capsule behaved in the same manner as under ambient conditions. | The capsule behaved in the same manner as under ambient conditions. | The capsule behaved in the same manner as under ambient conditions. |

FIGURE 3

| Physical manipulations performed after storage at 0 °C for 2 hours |||| 
| Method of Tampering |||| 
| Crushing | Grating | Grinding | Cutting |
| 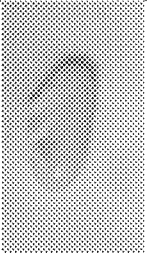 | 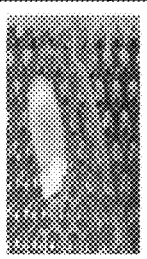 | 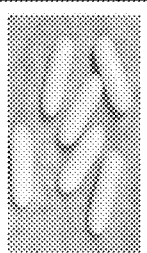 | 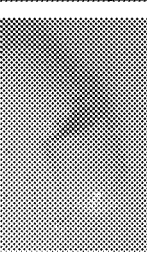 |
| The capsule behaved in the same manner as under ambient conditions. | The capsule behaved in the same manner as under ambient conditions. | The capsule behaved in the same manner as under ambient conditions. | The capsule behaved in the same manner as under ambient conditions. |

ABUSE-DETERRENT CONTROLLED RELEASE FORMULATIONS

CROSS REFERENCE TO RELATED APPLICATIONS

This application claims priority to U.S. Provisional Patent Application Nos. U.S. 61/976,237, filed on Apr. 7, 2014 and U.S. 62/101,431, filed on Jan. 9, 2015, both of which are incorporated by reference herein in their entirety. This application is related to International Patent Application No. PCT/US2015/24422 filed on Apr. 6, 2015, which is incorporated by reference herein in its entirety. This application is also related to U.S. patent application Ser. No. 14/679,233 and International Patent Application No. PCT/US2015/24464, both filed on Apr. 6, 2015, both of which are incorporated by reference herein in their entirety.

TECHNICAL FIELD

Described herein are abuse deterrent controlled release oral pharmaceutical compositions comprising and methods for making the same. In particular, an abuse deterrent controlled release oral pharmaceutical composition comprising a soft capsule and an abuse deterrent controlled release matrix comprising an active pharmaceutical ingredient are described.

BACKGROUND

Increased attention has been drawn to the recreational use and abuse of prescription pharmaceutical compositions. The abuse, or non-medicinal use, of prescription pharmaceutical compositions is an increasing problem. Accordingly, preventing the abuse of prescription pharmaceuticals through the development of abuse deterrent pharmaceutical compositions has become a high public health priority for the U.S. Food and Drug Administration (FDA). Prescription pharmaceutical compositions that are typically misused or abused fall, primarily, into three groups: (1) opioids prescribed for pain; (2) Central Nervous System (CNS) depressants prescribed for anxiety or sleep problems; and (3) stimulants, prescribed, for example, for attention deficit hyperactivity, narcolepsy, or obesity.

Methods for abusing prescription pharmaceutical compositions are varied and can include, for example, extraction, melting, volatilization, physical tampering (e.g., grinding, grating, crushing, etc.), or direct administration. For purposes of abuse, methods of administering active drug substances obtained from prescription pharmaceutical compositions or of the pharmaceutical compositions themselves are similarly diverse and include, for example, injection, smoking, snorting, swallowing, sublingual or buccal administration, chewing, or administration as an anal or vaginal suppository. Alcohol-induced "dose dumping," i.e., the rapid release of active pharmaceutical ingredients in the presence of a solvent such as ethanol, is also an abuse concern and safety issue.

There are a number of strategies for preventing the abuse of pharmaceuticals. Physical and chemical barriers can prevent the extraction of the drug or change the form of the drug making it less likely to be abused. Combinations of agonists and antagonists can be used, wherein the antagonist is only released upon product manipulation or tampering. Another strategy is to use aversives, compounds that produce an unpleasant effect when the dosage form is tampered with. In addition, prodrugs can be used, which are only changed into the active form of the drug in the gastrointestinal tract. The pharmaceutical industry is utilizing these strategies to develop abuse-deterrent pharmaceutical compositions in order to reduce the potential for misuse of prescription pharmaceutical compositions.

Accordingly, there is a need for abuse deterrent pharmaceutical compositions that have controlled release properties. The matrix formulations described herein minimize the likelihood of tampering, "dose dumping," or the extraction of active pharmaceutical ingredients from the composition.

SUMMARY

Described herein are pharmaceutical compositions comprising abuse deterrent controlled release matrices comprising active pharmaceutical ingredients. The matrix is structured to prevent extraction of the active pharmaceutical ingredients.

One embodiment described herein is an abuse deterrent oral pharmaceutical composition comprising a tamper resistant controlled release matrix comprising: (a) at least one lipid or lipophilic vehicle; (b) at least one hydrophilic polymer; (c) at least one hygroscopic polymer; and (d) at least one active pharmaceutical ingredient; wherein the matrix is resistant to tampering and is encapsulated in a soft capsule shell.

In one embodiment, the abuse deterrent oral pharmaceutical compositions described herein further comprises at least one suspension agent. In one aspect, the suspension agent comprises fumed silica, fumed alumina, or mixtures thereof.

In one aspect, the lipid or lipophilic vehicle comprises about 25% to about 90% of the total matrix mass. In another aspect, the at least one hygroscopic polymer comprises from about 1% to about 10% of the total matrix mass. In another aspect, the at least one hydrophilic polymer comprises about 5% to about 17% of the total matrix mass. In another aspect, the at least one active pharmaceutical ingredient comprises about 1% to about 50% of the total matrix mass. In another aspect, the ratio of the active pharmaceutical ingredient percent mass to the matrix percent mass is about 1:100 to about 1:1.

In one aspect, the lipid or lipophilic vehicle comprises at least one liquid lipid or lipophilic vehicle and at least one semisolid lipid or lipophilic vehicle. In another aspect, the liquid lipid or lipophilic vehicle comprises: olive oil, sunflower oil, canola oil, palmitoleic acid, oleic acid, myristoleic acid, linoleic acid, arachidonic acid, paraffin oil, or mineral oil. In another aspect, the lipid or lipophilic vehicle comprises olive oil or soybean oil. In another aspect, the semisolid lipid or lipophilic vehicle comprises one or more of: polyethylene glycol glyceride ester, paraffin wax, or bee's wax. In another aspect, the lipid or lipophilic vehicle comprises soybean oil, a polyethylene glycol glyceride ester, and bee's wax. In another aspect, the polyethylene glycol glyceride esters comprises glycerol esters of saturated fatty acids of about 8 to about 18 carbon molecules in length. In another aspect, the lipid or lipophilic vehicle comprises about 48% to about 52% of the total matrix mass.

In one aspect, the hygroscopic polymer comprises one or more of: polyvinylpyrrolidone, copovidone, hydroxypropylmethylcellulose, hydroxypropylcellulose, ethyl cellulose, methylcellulose, or polyethylene oxide. In another aspect, the hygroscopic polymer comprises polyvinylpyrrolidone having a K value from about 70 to about 90.

In one aspect, the hydrophilic polymer comprises: polyhydroxylalkylenediamine, dimethylaminoethyl methacrylate copolymer, sodium carboxy methylcellulose, ethylenediamine, sodium alginate, carbomers, poly galacturonic acid, or acrylic methacrylate copolymers.

In one aspect, the active pharmaceutical ingredient comprises at least one of: oxycodone, morphine, morphine analogues, or morphine antagonists, tapentadol, codeine, morphine, methadone, fentanyl and analogs, opioid pain relievers: oxycodone hydrochloride, hydrocodone bitartrate, hydromorphone, oxymorphone, meperidine, propoxyphene, flunitrazepam, barbiturates, amytal, nembutal, seconal, phenobarbital; benzodiazepines, zolpidem, zaleplon, eszopiclone, amphetamines, methylphenidate, or a combination of any of the foregoing. In another aspect, the active pharmaceutical ingredient comprises tapentadol.

In one embodiment, the abuse deterrent controlled release matrix comprises: (a) a liquid lipid vehicle; (b) a semi solid lipid or lipophilic vehicle; (c) at least one ionic hydrophilic polymer; (d) at least one hydroscopic polymer; (e) a suspension agent; and (f) at least one active pharmaceutical ingredient.

In one embodiment, the abuse deterrent controlled release matrix comprises: (a) soybean oil; (b) polyethylene glycol glyceride ester; (c) bee's wax; (d) polyvinylpyrrolidone or polyethylene oxide; (e) hydroxypropylmethylcellulose; (f) carbomer polymer; (g) dimethylaminoethyl methacrylate copolymer; (h) fumed silica; and (i) tapentadol.

In one embodiment, the abuse deterrent controlled release matrix comprises: (a) about 45% to about 52% soybean oil; (b) about 1.5% to about 5% Gelucire® 43/01; (c) about 1.8% to about 4% bee's wax; (d) about 2% to about 8% Kollidon® 90 F; (e) about 0.5% to about 4% Carbopol® 971 A; (f) about 2% to about 8% EUDRAGIT® EPO; (g) about 0.5% to about 5% Aerosil 200; and (h) about 5% to about 30% tapentadol hydrochloride.

In one embodiment, the abuse deterrent controlled release matrix comprises: (a) about 45% to about 52% soybean oil; (b) about 1.8% to about 4% Gelucire® 43/01; (c) about 1.8% to about 4% bee's wax; (d) about 5% to about 15% polyethylene oxide; (e) about 0.5% to about 4% Carbopol® 971 A; (f) about 2% to about 8% EUDRAGIT® EPO; (g) about 0.5% to about 5% Aerosil 200; and (h) about 5% to about 30% tapentadol hydrochloride.

In one embodiment, the abuse deterrent oral pharmaceutical compositions described herein further comprise at least one non-ionic surfactant; and at least one pH-buffering agent. In one aspect, the non-ionic surfactant comprises from about 1% to about 15% of the total matrix mass. In one aspect, the non-ionic surfactant comprises at least one of Pluronic®, Tween® 80, Span® 80, IGEPAL®, or Triton™ X-100. In another aspect, the non-ionic surfactant comprises from about 4% to about 7% of the total mass of the matrix. In another aspect, the non-ionic surfactant comprises an HLB value of about 1 to about 25 and a melting point temperature of about 30° C. to about 70° C. In another aspect, the pH-buffering agent comprises about 0.5% to about 8% of the total matrix mass. In another aspect, the pH-buffering agent comprises at least one of N-methyl-D-glucamine, di-isopropanol amine, tri-isopropanol amine, triethanolamine, tetrahydroxypropyl ethylenediamine, amino methyl propanol, amino acids, or other pharmaceutically acceptable buffering agents.

In one embodiment, the abuse deterrent controlled release matrix comprises: (a) olive oil; (b) a polyethylene glycol glyceride ester; (c) a poloxamer non-ionic surfactant; (d) a polyvinylpyrrolidone; (e) a carbomer polymer; (f) dimethylaminoethyl methacrylate copolymer; (g) N-methyl-D-glucamine; and (h) tapentadol.

In one embodiment, the abuse deterrent controlled release matrix comprises: (a) about 30% to about 40% olive oil; (b) about 7% to about 15% Gelucire® 43/01; (c) about 1% to about 10% Pluronic® F127; (d) about 2% to about 8% Kollidon® 90 F; (e) about 1% to about 6% Carbopol® 971 A; (f) about 2% to about 8% EUDRAGIT® EPO; (g) about 0.5% to about 6% N-methyl-D-glucamine; and (h) about 2.9% tapentadol hydrochloride.

In one embodiment, the soft capsule shell comprises a film forming polymer, a plasticizer, a solvent, optionally, an opacifying agent, a coloring agent, or a pharmaceutical excipient.

In one embodiment, the soft capsule shell comprises: (a) about 25-50% of at least one film-forming polymer; (b) about 15-25% of at least one plasticizer; (c) about 20-40% of a solvent; (d) optionally, an opacifying agent, a coloring agent, a pharmaceutical excipient, or combination thereof.

In one embodiment, the soft capsule shell comprises: (a) about 43% of at least one film-forming polymer; (b) about 20% of at least one plasticizer; (c) about 37% of a solvent; (d) optionally, about 0.7% of an opacifying agent; and (e) optionally, about 0.1% at least one coloring agent.

In one embodiment, the soft capsule shell comprises gelatin, glycerol, water, titanium oxide, and a coloring agent.

One embodiment described herein is a method for manufacturing an oral abuse deterrent controlled release controlled release soft capsule shell and matrix comprising: (a) providing a matrix as described in the embodiments and aspects herein; (b) providing a soft capsule gel mass as described in the embodiments and aspects herein; (c) casting the soft capsule gel mas into films using heat-controlled drums or surfaces; and (d) forming a soft capsule comprising the matrix composition using rotary die encapsulation technology. In one aspect, a soft capsule comprising an abuse deterrent controlled release matrix is produced by the methods of manufacturing described herein. In one aspect, an enteric soft capsule comprising an abuse deterrent controlled release matrix is produced by the methods of manufacturing described herein.

One embodiment described herein is an abuse deterrent oral pharmaceutical composition comprising a tamper resistant controlled release matrix comprising: (a) about 45% to about 52% soybean oil; (b) about 1.5% to about 5% polyethylene glycol glyceride ester (e.g., Gelucire® 43/01); (c) about 1.8% to about 4% bee's wax; (d) about 2% to about 8% polyvinylpyrrolidone (e.g., Kollidon® 90 F); (e) about 0.5% to about 4% carbomer (e.g., Carbopol® 971 A); (f) about 2% to about 8% dimethylaminoethyl methacrylate copolymer (e.g., EUDRAGIT® EPO); (g) about 0.5% to about 5% fumed silica (e.g., Aerosil 200); and (h) about 5% to about 30% tapentadol hydrochloride; wherein the matrix is resistant to tampering and has controlled release properties; the matrix being encapsulated in a soft capsule shell comprising: (i) about 25-50% gelatin; (j) about 15-25% glycerol (k) about 20-40% water; and (l) optionally, an opacifying agent, a coloring agent, a pharmaceutical excipient, or combination thereof.

One embodiment described herein is an abuse deterrent oral pharmaceutical composition comprising a tamper resistant controlled release matrix comprising: (a) about 45% to about 52% soybean oil; (b) about 1.8% to about 4% polyethylene glycol glyceride ester (e.g., Gelucire® 43/01); (c) about 1.8% to about 4% bee's wax; (d) about 5% to about 15% polyethylene oxide; (e) about 0.5% to about 4% carbomer (e.g., Carbopol® 971 A); (f) about 2% to about 8% dimethylaminoethyl methacrylate copolymer (e.g., EUDRAGIT® EPO); (g) about 0.5% to about 5% fumed silica (e.g., Aerosil 200); and (h) about 5% to about 30% tapentadol hydrochloride; wherein the matrix is resistant to tampering and has controlled release properties; the matrix being encapsulated in a soft capsule shell comprising: (i) about 25-50% gelatin; (j) about 15-25% glycerol (k) about 20-40% water; and (l) optionally, an opacifying agent, a coloring agent, a pharmaceutical excipient, or a combination thereof.

One embodiment described herein is an abuse deterrent oral pharmaceutical composition comprising a tamper resistant controlled release matrix comprising: (a) about 30% to about 40 olive oil; (b) about 7% to about 15% polyethylene glycol glyceride ester (e.g., Gelucire® 43/01); (c) about 1% to about 10% a poloxamer non-ionic surfactant (e.g., Pluronic® F127); (d) about 2% to about 8% polyvinylpyrrolidone (e.g., Kollidon® 90 F); (e) about 1% to about 6% carbomer (e.g., Carbopol® 971 A); (f) about 2% to about 8% dimethylaminoethyl methacrylate copolymer (e.g., EUDRAGIT® EPO); (g) about 0.5% to about 6% N-methyl-D-glucamine; and (h) about 30% tapentadol HCl; wherein the matrix is resistant to tampering and has controlled release properties; the matrix being encapsulated in a soft capsule shell comprising: (i) about 25-50% gelatin; (j) about 15-25% glycerol (k) about 20-40% water; and (l) optionally, an opacifying agent, a coloring agent, a pharmaceutical excipient, or a combination thereof.

One embodiment described herein is a method for treating, reducing the symptoms or onset of, or prophylaxis of pain stemming from diabetic neuropathy, chronic arthritis, osteoarthritis, rheumatoid arthritis, acute tendonitis, bursitis, headaches, migraines, chronic neuropathies, shingles, premenstrual symptoms, sports injuries, malignancy, radiculopathy, sciatica/sciatic pain, sarcoidosis, necrobiosis, lipoidica or granuloma annulare comprising administering to a subject in need thereof the pharmaceutical compositions described herein. In one aspect, the pharmaceutical composition comprises the soft capsule described herein.

One embodiment described herein is a method for reducing the ability of a subject to extract an active pharmaceutical ingredient from a pharmaceutical composition though crushing, grating, grinding, cutting, or solvating or dissolving the matrix comprising: providing the abuse deterrent matrix compositions and abuse deterrent oral pharmaceutical compositions described herein, wherein the composition is resistant to crushing, grating, grinding, cutting, solvation, or dissolution. In one aspect, the pharmaceutical composition comprises the soft capsule as described herein.

One embodiment described herein is a kit for dispensing providing the abuse deterrent matrix compositions and abuse deterrent oral pharmaceutical compositions described herein comprising: (a) at least one soft capsule comprising an abuse deterrent controlled release matrix comprising an active pharmaceutical ingredient; (b) at least one receptacle comprising a tamper evident, moisture proof packaging that reduces the ability of removing the oral pharmaceutical composition comprising blister or strip packs, aluminum blister, transparent or opaque polymer blister with pouch, polypropylene tubes, colored blister materials, tubes, bottles, and bottles optionally containing a child-resistant feature, optionally comprising a desiccant, such as a molecular sieve or silica gel; (c) optionally, an insert comprising instructions or prescribing information for the active pharmaceutical ingredient.

BRIEF DESCRIPTION OF THE DRAWINGS

FIG. 1. Physical manipulations of a soft capsule comprising the composition of Table 6 performed at ambient conditions (ca. 25° C.)

FIG. 2. Physical manipulations of a soft capsule comprising the composition of Table 6 performed after storage at 40° C. for 2 hours.

FIG. 3. Physical manipulations of a soft capsule comprising the composition of Table 6 performed after storage at 0° C. for 2 hours FIG. 4. Release profile of a soft capsule comprising the composition of Table 6 in 900 mL of simulated intestinal fluid at 100 rpm and 37° C.

DETAILED DESCRIPTION

Figure 4:
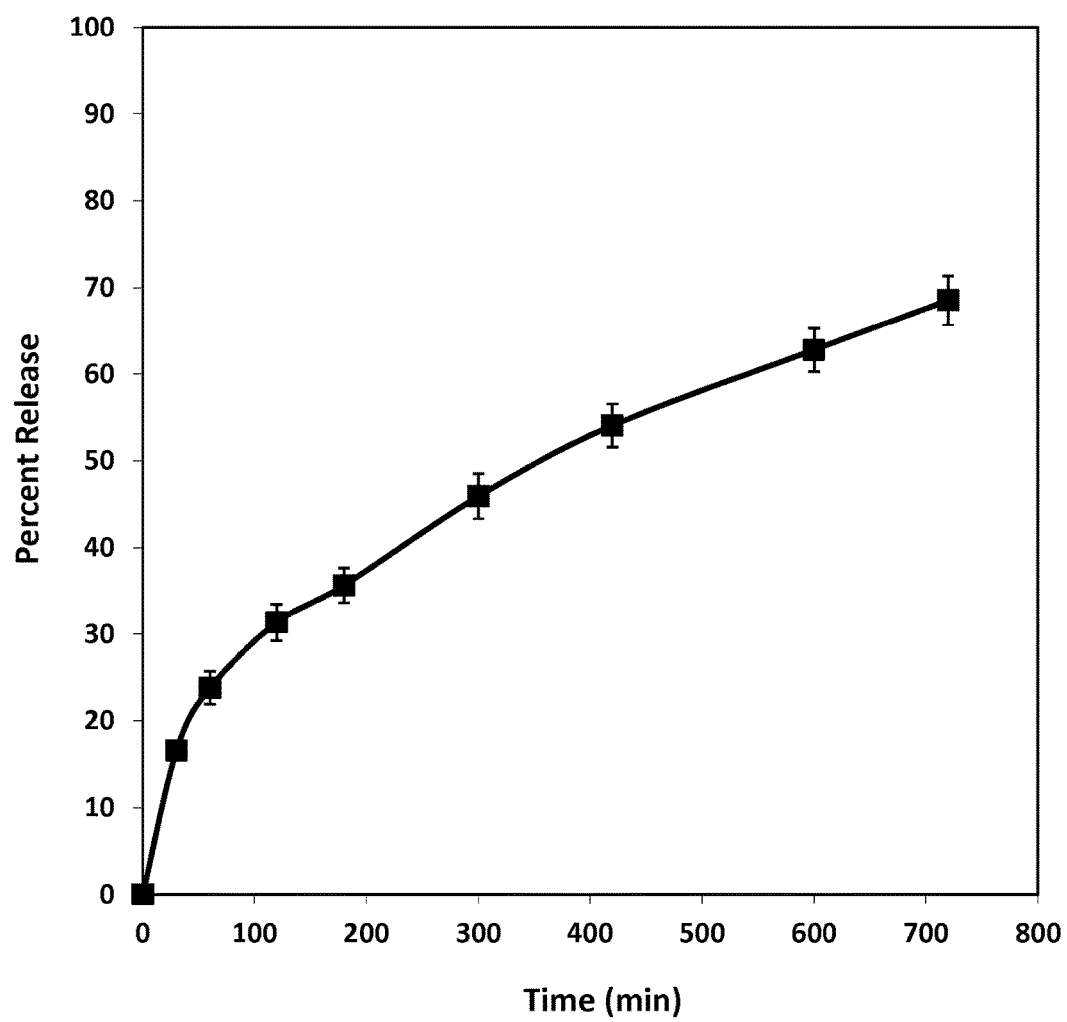

Described herein are abuse deterrent controlled release pharmaceutical compositions. The pharmaceutical compositions described herein provide abuse deterrent matrices and methods for preparation thereof. Also described herein are compositions and methods for manufacturing soft capsules comprising abuse deterrent controlled release pharmaceutical matrices. In some embodiments described herein, the soft capsule is an enteric soft capsule.

The term "abuse deterrent," as used herein, refers to a pharmaceutical composition that is resistant to tampering or accessing the active pharmaceutical ingredient for recreational drug use or drug abuse.

The phrase "recreational drug use," as used herein, refers to the voluntary use of an active pharmacetical agent or drug for a non-medical purpose to induce an effect, such as pleasure, satisfaction, euphoria, dissociation, or to enhance an experience.

The term "drug abuse," as use herein, refers to the habitual, compulsive, or recurrent use of an active pharmaceutical agent or drug, often despite negative consequences.

The term "tampering," as used herein, refers to any kind of actual or attempted physical manipulation or interference that may result in particle size reduction of a pharmaceutical composition. Tampering, as used herein also includes any actual or attempted dissolution or extraction of active pharmaceutical ingredients using solvents. Compositions that are resistant to physical tampering are formulated in such a way that the composition cannot readily reduced to a form that is suitable for abuse, such as, for example, injection or snorting, because the tablet cannot easily be ground, grated, dissolved, extracted, and the like at any temperature. Examples of physical tampering include, but are not limited to, crushing, grinding, grating, cutting, crisping, and other methods of particle size reduction. Dissolution tampering includes actual or attempted actions to dissolve or extract active pharmaceutical ingredients using aqueous or organic solvents such as water, ethanol, isopropanol, ethyl acetate, acetone, ether, or the like, at any temperature. Tampering, as used herein, includes "dose dumping."

The term "dose dumping" or "dumping" as used herein refers to the rapid release of the entire amount or a significant fraction of an active pharmaceutical ingredient or drug. Drug abusers often intentionally pursue dumping of a drug from the dosage form.

The terms "drug", "active ingredient," "active pharmaceutical ingredient," or "active pharmaceutical agent" as used herein refer to an agent, active ingredient, compound, or substance, compositions, or mixtures thereof, that provide a pharmacological, often beneficial, effect. Reference to a specific active ingredient includes, where appropriate, the active ingredient and any of its pharmaceutically acceptable salts or esters.

The terms "dosage" or "dose" denote any form of the active ingredient formulation that contains an amount sufficient to produce a therapeutic effect with a single administration. The dosage form used herein is for oral administration. The preferred oral dosage forms are soft capsules or enteric soft capsules.

The terms "active pharmaceutical ingredient load" or "drug load" as used herein refers to the quantity (mass) of the active pharmaceutical ingredient comprised in a single soft capsule fill.

The term "formulation" or "composition" as used herein refers to the active pharmaceutical ingredient or drug in combination with pharmaceutically acceptable excipients. This includes orally administrable formulations as well as formulations administrable by other means.

The term "titration" as used herein refers to the incremental increase in drug dosage to a level that provides the optimal therapeutic effect.

The term "controlled release" as used herein refers to a composition that does not immediately releases an active ingredient. "Controlled release" as used herein encompasses the terms "modified release," "sustained release," "extended release," and "delayed release."

The term "delayed release" as used herein refers to a composition that releases an active ingredient according to a desired profile over an extended period under physiological conditions or in an in vitro test. By "extended period" it is meant a continuous period of time of at least about 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours about 24 hours; or even longer.

The term "modified release" as used herein refers to a composition that releases an active ingredient at a slower rate than does an immediate release formulation under physiological conditions or in an in vitro test.

The term "sustained" release as used herein refers to a composition that releases an active ingredient over an extended period of time, for example minutes, hours, or days, such that less than all the active ingredient is released initially. A sustained release rate may provide, for example, a release of a certain specified amount of a drug or active ingredient from a dosage form, over a certain period, under physiological conditions or in an in vitro test.

The term "extended release" as used herein refers to a composition that releases an active ingredient over an extended period, such as of at least about 20 minutes, about 30 minutes, about 1 hour; about 2 hours; about 4 hours; about 6 hours; about 8 hours; about 10 hours; about 12 hours; about 14 hours; about 16 hours; about 18 hours; about 20 hours about 24 hours; or even longer; specifically over a period of at least 18 hours under physiological conditions or in an in vitro assay.

As used herein, the phrase "abuse deterrent controlled release" refers to a pharmaceutical composition comprising components or a formulation that prevents liberation of the active pharmaceutical ingredient(s) from the composition for potential abuse or dose dumping and the composition provides controlled release delivery of the active pharmaceutical ingredient upon ingestion of the composition by a subject.

The term "$C_{max}$" as used herein refers to the maximum observed blood (plasma, serum, or whole blood) concentration or the maximum blood concentration calculated or estimated from a concentration to time curve, and is expressed in units of mg/L or ng/mL, as applicable.

The term "$C_{min}$" as used herein refers to the minimum observed blood (plasma, serum, or whole blood) concentration or the minimum blood concentration calculated or estimated from a concentration to time curve, and is expressed in units of mg/L or ng/mL, as applicable.

The term "$C_{avg}$" as used herein refers to the blood (plasma, serum, or whole blood) concentration of the drug within the dosing interval, is calculated as AUC/dosing interval, and is expressed in units of mg/L or ng/mL, as applicable.

The term "$T_{max}$" as used herein refers to the time after administration at which $C_{max}$ occurs, and is expressed in units of hours (h) or minutes (min), as applicable.

The term "$AUC_{0 \to \tau}$" as used herein refers to area under the blood (plasma, serum, or whole blood) concentration versus time curve from time zero to time tau ($\tau$) over a dosing interval at steady state, where tau is the length of the dosing interval, and is expressed in units of h·mg/L or h·ng/mL, as applicable. For example, the term $AUC_{0 \to 12}$ as used herein refers to the area under the concentration versus time curve from 0 to 12 hours.

The term "$AUC_{0 \to \infty}$" as used herein refers to the area under the blood (plasma, serum, or whole blood) concentration versus time curve from time 0 hours to infinity, and is expressed in units of h·mg/L or h·ng/mL, as applicable.

The term "$AUC_{overall}$" as used herein refers to the combined area under the blood (plasma, serum, or whole blood) concentration versus time curve, and is expressed in units of h·mg/L (or h·ng/mL) for at least one or more doses of the pharmaceutical compositions described herein. In one aspect, the "$AUC_{overall}$" refers to the combined area under the blood concentration versus time curve for at least two doses of the pharmaceutical compositions described herein.

The term "treating" refers to administering a therapy in an amount, manner, or mode effective to improve a condition, symptom, or parameter associated with a disorder.

The term "prophylaxis" refers to preventing or reducing the progression of a disorder, either to a statistically significant degree or to a degree detectable to one skilled in the art.

The term "substantially" as used herein means to a great or significant extent, but not completely.

The term "about" as used herein refers to any value that is within a variation of up to ±10% of the value modified by the term "about."

As used herein, "a" or "an" means one or more unless otherwise specified.

Terms such as "include," "including," "contain," "containing," "has," or "having," and the like, mean "comprising."

The term "or" can be conjunctive or disjunctive.

Described herein are pharmaceutical compositions comprising abuse deterrent controlled release matrices comprising active pharmaceutical ingredients. The matrix is structured to prevent extraction of the active pharmaceutical ingredients.

In one embodiment, the pharmaceutical composition described herein comprises a soft capsule comprising an abuse deterrent controlled release matrix comprising an active pharmaceutical ingredient. In one embodiment, the active pharmaceutical ingredient is an analgesic. In another embodiment, the active pharmaceutical ingredient is an opiod analgesic.

In another embodiment, the soft capsule comprising a matrix can provide controlled release properties. Such controlled release matrix fills are described in International Patent Application Publication No. WO 2005/009409 and U.S. Patent Application Publication No. US 2006/0115527, both of which are incorporated by reference herein for such teachings. In one aspect, the soft capsule and matrix can be configured to provide controlled release, extended release, sustained release, delayed release, or combinations thereof.

In other embodiments, the pharmaceutical composition described herein comprises abuse deterrent properties. These abuse deterrent properties reduce the likelihood that the active pharmaceutical ingredient can be extracted from the composition through mechanisms, including but not limited to crushing, grating, grinding, cutting of the matrix, to permit solvation or extraction of the active pharmaceutical ingredient. In addition, the abuse deterrent properties reduce the likelihood that the active pharmaceutical ingredient can be extracted from the composition by dissolving or extracting in ethanol solutions of about 1% to about 50%, dissolving in solutions having pH values from about 1 to about 12, or dissolving in household chemical compositions, including water, coffee, vinegar, cola, milk, ethanol, isopropanol, acetone, ethyl acetate, or other common solvents.

In other embodiments described herein, the matrix comprises a lipid or lipophilic vehicle that provides a suspension of the active pharmaceutical ingredient. In one aspect, a soft capsule comprising an active pharmaceutical ingredient provides controlled release of the active pharmaceutical ingredient.

In other embodiments described herein, the pharmaceutical composition provides matrix fills for the active pharmaceutical ingredient, or derivatives thereof, based on lipids or lipophilic materials. The matrices described herein have a hydrophobic (lipophilic) surface in contact with a hydrophilic soft capsule shell to minimize any potential shell-fill interactions, such as when the soft capsules are filled with hydrophilic materials. In one embodiment described herein are methods for manufacturing matrix fills comprising an abuse deterrent controlled release matrix comprising an active pharmaceutical ingredient in a soft capsule in the form of a suspension, where part or all of the active pharmaceutical ingredient is suspended within the matrix. In one embodiment described herein is a soft capsule having a shell and an abuse deterrent controlled release matrix fill, wherein the matrix includes an active pharmaceutical ingredient suspended as solid particles within the lipophilic vehicle.

In one embodiment described herein, an exemplary abuse deterrent controlled release matrix has the composition of Table 1, including all possible iterations of the specified ranges that provide 100% for the total weight percentage, including or excluding the optional colorings, flavorings, or excipients.

TABLE 1

Exemplary Abuse Deterrent Controlled Release Matrix Composition

| Component | Exemplary Components | Composition Range (%) |
|---|---|---|
| Lipid or lipophilic vehicle(s) | Liquid lipid vehicle (LLV) and/or Semisolid lipid vehicle (SLV): soybean oil, bee's wax | 31-92 (LLV: 25-60/SLV: 6-32) |
| Non-ionic surfactant(s) | Pluronic ® F127, poloxamer, Tween ® 80, Triton ™ X | 1-15 |
| Hygroscopic polymer(s) | Polyvinylpyrrolidone (copovidone), ethyl cellulose, hydroxyproply methylcellulose, polyethylene oxide | 1-10 |
| Hydrophilic polymer(s) | Carbopol, Eudragit ®, Ethylenediamine | 2-20 |
| Suspension agent(s) | Fumed silica, Aerosil ® | 0.5-5 |
| pH buffering agent(s) | Triethanolamine, N-methyl-D-glucamine, Tromethamine | 1-8 |
| Active pharmaceutical ingredient(s) | Oxycodone, Tapentadol, Amytal | 5-50 |

In another embodiment, the lipid or lipophilic vehicle can be a liquid lipophilic vehicle, a semisolid lipophilic vehicle, or a mixture thereof. Suitable lipid or lipophilic vehicles include mineral oil; light mineral oil; natural oils (e.g., vegetable, corn, canola, sunflower, soybean, olive, coconut, cocoa, peanut, almond, cottonseed, persic, sesame, squalane, castor, cod liver, etc) hydrogenated vegetable oil; partially hydrogenated oils; bee's wax (beeswax); polyethoxylated bee's wax; paraffin; normal waxes; medium chain medium chain monoglycerides, diglycerides and triglycerides; higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol mono-oleate esters; glycerol mono-caprate; glyceryl monocaprylate; propylene glycol dicaprylate; propylene glycol monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyldodecanol; myristyl alcohol; isopropyl myristate, isopropyl palmitate, stearic acid, stearyl alcohol, and others known in the art.

In one embodiment, the lipid or lipophilic vehicle comprises a liquid lipophilic vehicle and a semisolid lipophilic vehicle. In one embodiment, the liquid lipid or lipophilic vehicle can be olive oil, sunflower oil, canola oil, palmitoleic acid, oleic acid, myristoleic acid, linoleic acid, arachidonic acid, paraffin oil, or mineral oil. In another embodiment, the semi-solid lipophilic vehicle can be a polyethylene glycol glyceride ester, paraffin wax, or bee's wax. In another embodiment, the semi-solid lipophilic vehicle is Gelucire® 33/01, Gelucire® 37/02, Gelucire® 39/01, Gelucire® 43/01, Gelucire® 44/14, Gelucire® 50/02, Gelucire® 50/13, Gelucire® 53/10, or Gelucire® 62/02. In one aspect, the liquid lipid or lipophilic vehicle is olive oil. In another aspect, the semisolid lipid or lipophilic vehicle comprises a Gelucire®. In another aspect, the semisolid lipid or lipophilic vehicle comprises bee's wax. In one aspect, the Gelucire® semisolid lipid vehicle has a HLB value of about 1 and a melting point of about 43. In one aspect, the semisolid lipid or lipophilic vehicle is Gelucire® 43/01.

In one embodiment, the matrix comprises a hydrophilic ionic polymer. In one embodiment, the hydrophilic polymers comprise polyhydroxyalkylenediamine, dimethylaminoethyl methacrylate copolymer, Poly(butyl methacrylate-co-(2-dimethylaminoethyl) methacrylate-co-(2-dimethylaminoethyl) 1:2:1 (Eudragit® EPO); sodium carboxy methylcellulose, carboxymethyl cellulose ethylenediamine, sodium alginate, alginic acid, pectin, carbomers, Carbopol® copolymers (polyacrylic acid polymers), such as Carbopol® 934, Carbopol® 940, Carbopol® 941 or Carbopol® 974P; a Pemulen® polymer; polycarbophil poly galacturonic acid, polyglucoronic acid, chondroitic sulfate, carrageenan, and acrylic methacrylate copolymers. In one aspect, the hydrophilic polymer swells in aqueous media. In another aspect, the hydrophilic polymers swell at a pH of about 4 to about 6. In another embodiment, one or more hydrophilic ionic polymers form ionic interactions. In another embodiment, the matrix comprises anionic polymers, cationic polymers, or mixtures thereof. In another embodiment, a hydrophilic cationic polymer and a hydrophilic anionic polymer are combined to form an ionic polymer complex or network. In one aspect, the hydrophilic ionic polymer is Carbopol® 971A. In another aspect, the hydrophilic ionic polymer is Eudragit® EPO.

In one embodiment, the matrix comprises a non-ionic surfactant. The surfactant can have a hydrophilic/lipophilic balance (HLB) value between about 1 and about 25 and a melting point between about 25° C. and about 70° C. The HLB characteristic of surfactants can be determined in accordance with "Physical Pharmacy: Physical Chemical Principles in the Pharmaceutical Sciences," Fourth Edition, pp. 371-373, A. Martin, Ed., Lippincott Williams & Wilkins, Philadelphia (1993). Suitable non-ionic surfactants include: Pluronic® 10R5, Pluronic® 17R2, Pluronic® 17R4, Pluronic® 25R2, Pluronic® 25R4, Pluronic® 31R1, Pluronic® F 108, Pluronic® F 108 NF, Pluronic® F 108, Pluronic® F 108NF, Poloxamer 338, Pluronic® F 127, Pluronic® F 127 NF, Pluronic® F 127 NF 500 BHT Prill, Pluronic® F 127 NF Prill, Poloxamer 407, Pluronic® F 38, Pluronic® F 38 Pastille, Pluronic® F 68, Pluronic® F 68 LF Pastille, Pluronic® F 68 NF, Pluronic® F 68 NF Prill, Poloxamer 188, Pluronic® F 68 Pastille, Pluronic® F 77, Pluronic® F 77 Micropastille, Pluronic® F 87, Pluronic® F 87 NF, Pluronic® F 87 NF Prill, Poloxamer 237, Pluronic® F 88, Pluronic® F 88 Pastille, Pluronic® F 98, Pluronic® L 10, Pluronic® L 101, Pluronic® L 121, Pluronic® L 31, Pluronic® L 35, Pluronic® L 43, Pluronic® L 61, Pluronic® L 62, Pluronic® L 62 LF, Pluronic® L 62D, Pluronic® L 64, Pluronic® L 81, Pluronic® L 92, Pluronic® N 3, Pluronic® P 103, Pluronic® P 104, Pluronic® P 105, Pluronic® P 123 Surfactant, Pluronic® P 65, Pluronic® P 84, Pluronic® P 85, Adogen® 464, Alkanol® 6112, Brij® 52, Brij® 93, Brij® S2, Brij® S, Brij® 58, Brij® C10, Brij® L4, Brij® O10, Brij® O10, BRIJ® O20, Brij® S10, Brij® S20, ethylenediamine tetrakis(ethoxylate-block-propoxylate) tetrol, ethylenediamine tetrakis(ethoxylate-block-propoxylate) tetrol, ethylenediamine tetrakis(propoxylate-block-ethoxylate) tetrol, IGEPAL® CA-210, IGEPAL® CA-520, IGEPAL® CA-720, IGEPAL® CO-520, IGEPAL® CO-630, IGEPAL® CO-720, IGEPAL® CO-890, IGEPAL® DM-970, MERPOL® DA, MERPOL® HCS, MERPOL® OJ, MERPOL® SE, MERPOL® SH, MERPOL® A, Poly(ethylene glycol) sorbitan tetraoleate, poly(ethylene glycol) sorbitol hexaoleate, poly(ethylene glycol) (12), poly(ethylene glycol) (18), polyethylene-block-poly(ethylene glycol), sorbitan monopalmitate, 2,4,7,9-tetramethyl-5-decyne-4,7-diol ethoxylate, Nonidet™ P-40, Triton™ N-101, Triton™ X-100, Triton™ X-114, Triton™ X-405, TWEEN® 20, TWEEN® 40, TWEEN® 60, TWEEN® 85, Zonyl® FS-300, or Zonyl® FSN. In one embodiment, the non-ionic surfactant comprises Pluronic® F127, Tween® 80, Span® 80, IGEPAL®, or Triton™ X-100. In one aspect, the non-ionic surfactant comprises a poloxamer. In one aspect, the non-ionic surfactant comprises Pluronic® F127.

In another embodiment, the matrix comprises a hygroscopic polymer. In one embodiment, the hygroscopic polymers include polyvinylpyrrolidone, copovidone, hydroxypropylmethylcellulose, hydroxypropylcellulose, ethyl cellulose, methylcellulose, and polyethylene oxide. Suitable hygroscopic polymers include polyvinyl alcohol, a copolymer of polyvinylpyrrolidone and polyvinyl acetate, hydroxypropyl cellulose, hydroxypropyl methylcellulose, hydroxyethyl cellulose, hydroxymethyl cellulose, gelatin, polyethylene oxide, such as POLYOX™ 100,000-600,000 MW, acacia, dextrin, starch, polyhydroxyethylmethacrylate, a water-soluble non-ionic polymethacrylate or copolymer thereof, a modified cellulose, a modified polysaccharide, a non-ionic gum, or a non-ionic polysaccharide. In one aspect, the hygroscopic polymer is polyvinylpyrrolidone. In one aspect, the hygroscopic polymer comprises Kollidon® 90 F. In one aspect, the hygroscopic polymer comprises a cellulose polymer. In one aspect, the hygroscopic polymer comprises hydroxypropylmethylcellulose (e.g., HPMC 4M). In another aspect, the hygroscopic polymer is a polyethylene oxide polymer (e.g., POLYOX™ 100,000).

In another embodiment, the matrix comprises a pH buffering agent. Suitable pharmaceutically acceptable buffering agents comprise arginine, aminomethyl propanol, tetrahydroxypropyl ethylenediamine, triethanolamine, tromethamine, PEG-15 cocamine, di-isopropanol amine, tri-isopropanol amine, N-methyl-D-glucamine, glycine, malate, tartarate, lactate, citrate, acetate, sodium bicarbonate, sodium phosphate, or other buffering agents, having $pK_a$s at any physiologically acceptable pH, generally from about pH 4 to about pH 7. Amino acids or other physiological metabolites may be used as buffering agents. A combination of buffering agents may also be employed, such as phosphate and acetate, and the like. In one aspect, the pH buffering agent is N-methyl-D-glucamine (e.g., meglumine).

In another embodiment, the matrix comprises a neutralizing agent. Suitable pharmaceutically acceptable neutralizing agents comprise HCl, phosphoric acid, carbonic acid, sodium hydroxide, ammonium hydroxide, potassium hydroxide, sodium bicarbonate, sodium carbonate, and the like.

In another embodiment, the matrix comprises a suspension agent. Suitable pharmaceutically acceptable suspension agents comprise fumed silicon dioxide, such as Aerosil® 90, Aerosil® 130, Aerosil® 150, Aerosil® 200, Aerosil® 255, Aerosil® 300, Aerosil® 380, Aerosil® OX 50, Aerosil® TT 600, Aerosil® 200 F, Aerosil® 380 F, Aerosil® 200 Pharma Aerosil® 300 Pharma, Aeropearl® 300/30, or Aeropearl® 300 Pharma. In one aspect, the suspension agent comprises Aerosil® 200.

In another embodiment, the matrix can include a hydrophilic internal phase and a lipid or lipophilic external phase. The internal phase can also be structured. A "structured" internal phase, as used herein, means a solid, semisolid, or a gel whose shape is relatively stable and does not usually aggregate to form a large globule. A structured internal phase therefore provides controlled drug release and stabilizes the physical state of the matrix. Without being bound to any theory, it is believed that the structured nature of the matrix impedes solvation and/or diffusion of the active pharmaceutical ingredient out of the matrix.

In another embodiment, the active pharmaceutical ingredient can be dispersed in the internal phase as a suspension form. In another embodiment, the active pharmaceutical ingredient can be dispersed in the internal phase as a solid form.

In one embodiment described herein, the matrix may comprise one or more lipid or lipophilic vehicles, one or more hydrophilic polymers, one or more hygroscopic polymers, one or more suspension agents, optionally, one or more non-ionic surfactants, optionally, one or more pH buffering agent, and one or more active pharmaceutical ingredients. Without being bound to any theory, it is believed that the hydrophilic cationic and anionic polymers described herein combine within the matrix to form polymer networks or complexes comprising ionic interactions. Further, without being bound to any theory, it is believed that the ionic polymer network swells when hydrated with an aqueous solution and the swelling impedes the dissolution and/or diffusion of the active pharmaceutical ingredient out of the matrix. Without being bound by any theory, it is believed that non-ionic surfactants and hygroscopic polymers facilitate hydration of the hydrophilic ionic polymers described herein. Moreover, without being bound to any theory, the lipid or lipophilic vehicle of the matrix further prevents diffusion and/or solvation of the active pharmaceutical ingredient. Without being bound to any theory, it is believed that the suspension agents prevent precipitation of the active pharmaceutical ingredient or other matrix components. The matrix compositions described herein permit abuse deterrence by preventing liberation of the active ingredient for injection or insufflation and prevent solvation, dissolution, or extraction of the active pharmaceutical ingredient by use of aqueous or organic solutions. Furthermore, the matrix compositions also provide controlled release delivery of the active pharmaceutical ingredient after ingestion by a subject.

In another embodiment, the lipid or lipophilic vehicle comprises a liquid lipid or lipophilic vehicle, a semisolid lipid or lipophilic vehicle, or a combination thereof. In one embodiment, the total lipid or lipophilic vehicle comprises one or more liquid lipid vehicles and one or more semi-solid lipid vehicles. In one embodiment, the total lipid or lipophilic vehicle comprises about 30% to about 92% of the total matrix mass including all integers within the specified range. The total lipid or lipophilic vehicle comprises about 30%, about 35%, about 40%, about 45%, about 50%, about 55%, about 60%, about 65%, about 70%, about 75%, about 80%, about 85%, or about 90% of the total matrix mass. In one embodiment, the total lipid or lipophilic vehicle comprises about 40% to about 55% of the total matrix mass including all integers within the specified range. In one embodiment, the total lipid or lipophilic vehicle comprises about 50% to about 55% of the total matrix mass including all integers within the specified range. In one aspect, the total lipid or lipophilic vehicle comprises about 55% of the total matrix mass. In another aspect, the total lipid or lipophilic vehicle comprises about 53% of the total matrix mass. In another aspect, the total lipid or lipophilic vehicle comprises about 50% of the total matrix mass. In another aspect, the total lipid or lipophilic vehicle comprises about 49% of the total matrix mass.

In another embodiment, one or more liquid lipid or lipophilic vehicles comprise from about 25% to about 60% of the total matrix mass including all integers within the specified range. The one or more lipid or lipophilic vehicles comprise about 25%, about 30%, about 32%, about 34%, about 36%, about 38%, about 40%, about 42%, about 45%, about 50%, about 55%, or about 60% of the total matrix mass. In one embodiment, the total liquid lipid or lipophilic vehicle comprises from about 38% to about 52% of the total matrix mass including all integers within the specified range. In one aspect, the total liquid lipid or lipophilic vehicle comprises about 38% of the total matrix mass. In one aspect, the total liquid lipid or lipophilic vehicle comprises about 46% of the total matrix mass. In one aspect, the total liquid lipid or lipophilic vehicle comprises about 50% of the total matrix mass.

In another embodiment, one or more semisolid lipid or lipophilic vehicles comprise from about 4% to about 32% of the total matrix mass including all integers within the specified range. The one or more semisolid lipid or lipophilic vehicles comprise about 4%, about 5%, about 6%, about 7%, about 8%, about 9%, about 10%, about 12%, about 15%, about 18%, about 20%, about 22%, about 25%, about 28%, about 30%, or about 32% of the total matrix mass. In one embodiment, the total semisolid lipid or lipophilic vehicle comprises from about 4% to about 15% of the total matrix mass including all integers within the specified range. In one aspect, the total semisolid lipid or lipophilic vehicle comprises about 14% of the total matrix mass. In one aspect, the total semisolid lipid or lipophilic vehicle comprises about 11% of the total matrix mass. In one aspect, the total semisolid lipid or lipophilic vehicle comprises about 8% of the total matrix mass. In one aspect, the total semisolid lipid or lipophilic vehicle comprises about 6% of the total matrix mass. In one aspect, the total semisolid lipid or lipophilic vehicle comprises about 4% of the total matrix mass.

In another embodiment, the ratio of the liquid lipid vehicle to semisolid lipid ranges from about 2:1 to about 14:1, including all iterations of ratios within the specified range. In one embodiment, the ratio of the lipid liquid to semisolid liquid ranges from about 2.5:1 to about 13:1, including all iterations of ratios within the specified range. In one aspect, the ratio of the lipid liquid to semisolid liquid is about 13:1. In one aspect, the ratio of the lipid liquid to semisolid liquid is about 8:1. In one aspect, the ratio of the lipid liquid to semisolid liquid is about 7:1. In one aspect, the ratio of the lipid liquid to semisolid liquid is about 6:1. In one aspect, the ratio of the lipid liquid to semisolid liquid is about 5:1. In one aspect, the ratio of the lipid liquid to semisolid liquid is about 4:1. In one aspect, the ratio of the lipid liquid to semisolid liquid is about 3:1. In one aspect, the ratio of the lipid liquid to semisolid liquid is about 2:1.

In another embodiment, the one or more hygroscopic polymers comprise from about 1% to about 25% of the total matrix mass including all integers within the specified range. The one or more hygroscopic polymers comprise about 1%, about 2%, about 3%, about 4%, about 5%, about 6%, about 7%, about 8%, about 9%, about 10%, about 12%, about 15%, about 18%, about 20%, about 22%, or about 25% of the total matrix mass. In another embodiment, the total hygroscopic polymer content comprises from about 5% to about 18% of the total matrix mass including all integers within the specified range. In another embodiment, the total hygroscopic polymer content comprises from about 10% to about 16% of the total matrix mass including all integers within the specified range. In one aspect, the total hygroscopic polymer content comprises about 20% of the total matrix mass. In one aspect, the total hygroscopic polymer content comprises about 18% of the total matrix mass. In one aspect, the total hygroscopic polymer content comprises about 16% of the total matrix mass. In one aspect, the total hygroscopic polymer content comprises about 15% of the total matrix mass. In one aspect, the total hygroscopic polymer content comprises about 13% of the total matrix mass. In one aspect, the total hygroscopic polymer content comprises about 12% of the total matrix mass. In one aspect, the total hygroscopic polymer content comprises about 11% of the total matrix mass. In one aspect, the total hygroscopic polymer content comprises about 10% of the total matrix mass. In one aspect, a hygroscopic polymer comprises about 9% of the total matrix mass. In one aspect, a hygroscopic polymer comprises about 8% of the total matrix mass. In one aspect, a hygroscopic polymer comprises about 7% of the total matrix mass. In one aspect, a hygroscopic polymer comprises about 6% of the total matrix mass. In one aspect, a hygroscopic polymer comprises about 5% of the total matrix mass. In one aspect, a hygroscopic polymer comprises about 4% of the total matrix mass.

In another embodiment, the matrix comprises a non-ionic surfactant. In another embodiment, the non-ionic surfactant comprises from about 1% to about 15% of the total matrix mass including all integers within the specified range. In another embodiment, non-ionic surfactant comprises from about 2.5% to about 10% of the total matrix mass including all integers within the specified range. In one aspect, non-ionic surfactant comprises about 2.5% of the total matrix mass. In one aspect, the non-ionic surfactant comprises about 6.5% of the total matrix mass. In one aspect, the non-ionic surfactant comprises about 8.5% of the total matrix mass.

In another embodiment, the total amount of hygroscopic polymer and non-ionic surfactant ranges from about 4% to about 20% of the total matrix mass including all integers within the specified range. In one aspect, the total amount of hygroscopic polymer and non-ionic surfactant comprises about 6% of the total matrix mass. In one aspect, the total amount of hygroscopic polymer and non-ionic surfactant comprises about 10% of the total matrix mass. In one aspect, the total amount of hygroscopic polymer and non-ionic surfactant comprises about 18% of the total matrix mass.

In another embodiment, the ratio of the non-ionic surfactant to the hygroscopic polymer ranges from about 0.2:1 to about 15:1, including all iterations of ratios within the specified range. In another embodiment, the ratio of the non-ionic surfactant to the hygroscopic polymer ranges from about 0.2:1 to about 5:1, including all iterations of ratios within the specified range. In one aspect, the ratio of the non-ionic surfactant to the hygroscopic polymer is about 0.7:1. In one aspect, the ratio of the non-ionic surfactant to the hygroscopic polymer is about 1.5:1. In one aspect, the ratio of the non-ionic surfactant to the hygroscopic polymer is about 3.5:1.

In another embodiment, the ratio of lipophilic vehicle to the hygroscopic polymer and non-ionic surfactant ranges from about 2:1 to about 20:1, including all iterations of ratios within the specified range. In another embodiment, the ratio of lipophilic vehicle to the hygroscopic polymer and non-ionic surfactant ranges from about 2:1 to about 10:1, including all iterations of ratios within the specified range. In one aspect, the ratio of the lipophilic vehicle to the hygroscopic polymer and non-ionic surfactant is about 3:1. In one aspect, the ratio of the lipophilic vehicle to the hygroscopic polymer and non-ionic surfactant is about 4:1. In one aspect, the ratio of the lipophilic vehicle to the hygroscopic polymer and non-ionic surfactant is 4.2:1. In one aspect, the ratio of the lipophilic vehicle to the hygroscopic polymer and non-ionic surfactant is 3.4:1.

In another embodiment, the matrix comprises a hydrophilic polymer. In one aspect, the hydrophilic polymer is a non-ionic polymer, an anionic polymer, a cationic polymer, or a combination thereof. In one aspect, the matrix comprises a hydrophilic anionic polymer. In another aspect, the matrix comprises a hydrophilic cationic polymer. In another aspect, the matrix comprises a hydrophilic anionic polymer and hydrophilic cationic polymer.

In another embodiment, the hydrophilic polymer comprises from about 2% to about 20% of the total matrix mass including all integers within the specified range. The hydrophilic polymer comprises about 2%, about 3%, about 4%, about 5%, about 6%, about 7%, about 8%, about 9%, about 10%, about 12%, about 15%, about 18%, or about 20% of the total matrix mass. In one aspect, the hydrophilic polymer comprises about 10% of the total matrix mass. In one aspect, the hydrophilic polymer comprises about 9% of the total matrix mass. In one aspect, the hydrophilic polymer comprises about 8% of the total matrix mass. In one aspect, the hydrophilic polymer comprises about 7% of the total matrix mass. In one aspect, the hydrophilic polymer comprises about 6% of the total matrix mass. In one aspect, the hydrophilic polymer comprises about 5% of the total matrix mass. In one aspect, the hydrophilic polymer comprises about 4% of the total matrix mass.

In one embodiment, the matrix comprises multiple species of hydrophilic ionic polymers. In another embodiment, the matrix comprises two species of hydrophilic ionic polymers. In one embodiment, one species of hydrophilic polymer is one or more anionic polymers and the other species of hydrophilic polymer is one or more cationic polymers. In one embodiment, the ratio of one species of hydrophilic ionic polymer to a second hydrophilic ionic polymer is about 0.3:1 to about 1:1, including all iterations of ratios within the specified range. In one aspect, the ratio of one species of hydrophilic ionic polymer to a second hydrophilic ionic polymer is about 0.8:1. In one aspect, the ratio of one species of hydrophilic ionic polymer to a second hydrophilic polymer ionic is about 0.7:1. In one aspect, the ratio of one species of hydrophilic ionic polymer to a second hydrophilic polymer ionic is about 0.5:1. In one aspect, the ratio of one species of hydrophilic ionic polymer to a second hydrophilic polymer ionic is about 0.4:1. In one aspect, the ratio of one species of hydrophilic ionic polymer to a second hydrophilic polymer ionic is about 0.3:1. In one aspect, one hydrophilic polymer species is anionic, and the other hydrophilic polymer species is cationic.

In another embodiment, the matrix comprises a pH buffering agent. In one aspect, the pH buffering agent comprises a $pK_a$ from about pH 2.5 to about pH 12, including all integers within the specified range. In another aspect, the pH buffering agent comprises a $pK_a$ from about pH 5 to about pH 11. In another aspect, the pH buffering agent has a pK$_a$ of about 7.5 to about 10, including all integers within the specified range. In one aspect, the pH buffering agent has a pK$_a$ of about 9.

In one embodiment, the pH buffering agent comprises about 1% to about 8% of the total matrix mass including all integers within the specified range. In one aspect, the pH buffering agent comprises about 2% of the total matrix mass. In one aspect, the pH buffering agent comprises about 4% of the total matrix mass. In one aspect, the pH buffering agent comprises about 5.5% of the total matrix mass.

In some embodiments, the ratio of the pH buffering agent to the ionic hydrophilic polymers is from about 0.2:1 to about 3:1, including all iterations of ratios within the specified range. In some embodiments, the ratio of the pH buffering agent to the ionic hydrophilic polymers is from about 0.2:1 to about 0.5:1, including all iterations of ratios within the specified range. In one aspect, the ratio of the pH buffering agent to the ionic hydrophilic polymers is about 0.3. In one aspect, the ratio of the pH buffering agent to the ionic hydrophilic polymers is about 0.5.

The total hydrophilic composition of the matrix comprises one or more one or more hygroscopic polymers; one or more hydrophilic polymers; optionally, one or more non-ionic surfactants, and optionally, one or more pH buffering agents. In one embodiment, the total hydrophilic composition of the matrix comprises about 7% to about 48% of the total matrix mass including all integers within the specified range. In another embodiment, the total hydrophilic matrix composition comprises about 18% to about 32% of the total matrix mass including all integers within the specified range. In one embodiment, the total hydrophilic matrix composition comprises about 18% to about 22% of the total matrix mass including all integers within the specified range. In one aspect, the total hydrophilic matrix composition comprises about 18% of the total matrix mass. In one aspect, the total hydrophilic matrix composition comprises about 19% of the total matrix mass. In one aspect, the total hydrophilic matrix composition comprises about 20% of the total matrix mass. In one aspect, the total hydrophilic matrix composition comprises about 21% of the total matrix mass. In one aspect, the total hydrophilic matrix composition comprises about 22% of the total matrix mass.

In another embodiment, the ratio of the total lipid or lipophilic vehicle to the total hydrophilic matrix composition is from about 1:1 to about 13:1, including all iterations of ratios within the specified range. In another embodiment, the ratio of the lipid or lipophilic vehicle to the hydrophilic matrix composition is from about 1:1 to about 3:1, including all iterations of ratios within the specified range. In one aspect, the ratio of the lipid or lipophilic vehicle to the hydrophilic matrix composition is about 1.5:1. In one aspect, the ratio of the lipid or lipophilic vehicle to the hydrophilic matrix composition is about 2.5:1. In one aspect, the ratio of the lipid or lipophilic vehicle to the hydrophilic matrix composition is about 2.3:1. In one aspect, the ratio of the lipid or lipophilic vehicle to the hydrophilic matrix composition is about 2.7:1.

In another embodiment, the matrix comprises a suspension agent. In one embodiment, the suspension agent comprises about 0.5% to about 5% of the total matrix mass including all integers within the specified range. In one embodiment, the suspension agent comprises about 0.8% to about 2% of the total matrix mass including all integers within the specified range. In one aspect, the suspension agent comprises about 2% of the total matrix mass. In another aspect, the suspension agent comprises about 1.5% of the total matrix mass. In another aspect, the suspension agent comprises about 1.3% of the total matrix mass. In another aspect, the suspension agent comprises about 1.2% of the total matrix mass. In one aspect, the suspension agent comprises about 1.2% of the total matrix mass. In one aspect, the suspension agent comprises about 1% of the total matrix mass. In one aspect, the suspension agent comprises about 0.9% of the total matrix mass. In one aspect, the suspension agent comprises about 0.8% of the total matrix mass.

In one embodiment, the matrix comprises a lipid or lipophilic composition and hydrophilic composition. In one embodiment, the lipid or lipophilic composition comprises one or more liquid lipid vehicles and one or more semi-solid lipid vehicles and the hydrophilic composition comprises one or more hygroscopic polymers, one or more hydrophilic polymers. In another embodiment, the hydrophilic matrix composition comprises. In one embodiment, the matrix further comprises a suspension agent. In another embodiment, the matrix further comprises a non-ionic surfactant. In another embodiment, the matrix further comprises a pH buffering agent.

In one embodiment, the matrix comprises one or more liquid lipid vehicles, one or more semi-solid lipid vehicles, one or more one or more hygroscopic polymers, one or more hydrophilic polymers, one or more non-ionic surfactants, one or more pH buffering agents, and one or more active pharmaceutical ingredients. In one embodiment, the matrix comprises any one of the compositions of Tables 6, 13, or 15.

In one embodiment, the matrix comprises one or more liquid lipid vehicles, one or more semi-solid lipid vehicles, one or more one or more hygroscopic polymers, one or more hydrophilic polymers, one or more suspension agents, and one or more active pharmaceutical ingredients. In one embodiment, the matrix comprises any one of the compositions of Tables 7, 8, 14, or 16.

In one embodiment, the matrix comprises one or more active pharmaceutical ingredients (API). In one aspect, the active pharmaceutical ingredient is useful in treating pain. In one aspect, the active pharmaceutical ingredient is tapentadol, oxycodone, hydrocodeine, or codeine. In one aspect, the active pharmaceutical ingredient is tapentadol.

In another embodiment, the one or more active pharmaceutical ingredient comprises from about 1% to about 50% of the total matrix mass including all integers within the specified range. In another embodiment, the active pharmaceutical ingredient comprises from about 5% to about 30% of the total matrix mass including all integers within the specified range. In one aspect, the active pharmaceutical ingredient comprises about 5% of the total matrix mass. In one aspect, the active pharmaceutical ingredient comprises about 10% of the total matrix mass. In one aspect, the active pharmaceutical ingredient comprises about 15% of the total matrix mass. In one aspect, the active pharmaceutical ingredient comprises about 20% of the total matrix mass. In one aspect, the active pharmaceutical ingredient comprises about 25% of the total matrix mass.

In another embodiment, the ratio of the active pharmaceutical ingredient to the total hydrophilic composition of the matrix ranges from about 0.1:1 to about 2.6:1, including all iterations of ratios within the specified range. The ratio of the active pharmaceutical ingredient to the total hydrophilic composition of the matrix can be 0.1:1, 0.3:1, 0.5:1, 1:1, 1.1:1, 1.2:1, 1.3:1, 1.4:1, 1.8:1, 2:1, 2.4:1, or 2.6:1. In one aspect, the ratio of the active pharmaceutical ingredient to the total hydrophilic composition of the matrix is about 0.5:1. In one aspect, the ratio of the active pharmaceutical ingredient to the total hydrophilic composition of the matrix is about 1.8:1. In one aspect, the ratio of the active pharmaceutical ingredient to the total hydrophilic composition of the matrix t is about 1.6:1. In one aspect, the ratio of the active pharmaceutical ingredient to the total hydrophilic composition of the matrix is about 1.2:1. In one aspect, the ratio of the active pharmaceutical ingredient to the total hydrophilic composition of the matrix is about 1.4:1.

In another embodiment, the ratio of the active pharmaceutical ingredient to the total lipid or lipophilic composition of the matrix ranges from about 0.2:1 to about 1.8:1, including all iterations of ratios within the specified range. The ratio of the active pharmaceutical ingredient to the total lipid or lipophilic composition of the matrix can be 0.1:1, 0.2:1, 0.5:1, 0.6:1, 0.8:1, 0.9:1, 1:1, 1.2:1, 1.4:1, or 1.8:1. In one aspect, the ratio of the active pharmaceutical ingredient to the total lipid or lipophilic composition of the matrix is about 1.4:1. In one aspect, the ratio of the active pharmaceutical ingredient to the total lipid or lipophilic composition of the matrix is about 1:1. In one aspect, the ratio of the active pharmaceutical ingredient to the total lipid or lipophilic composition of the matrix t is about 0.8:1. In one aspect, the ratio of the active pharmaceutical ingredient to the total lipid or lipophilic composition of the matrix is about 0.6:1. In one aspect, the ratio of the active pharmaceutical ingredient to the total lipid or lipophilic composition of the matrix is about 0.5:1.

In another embodiment, the ratio of the active pharmaceutical ingredient to the total matrix composition ranges from about 0.1:1 to about 1:1, including all iterations of ratios within the specified range. The ratio of the active pharmaceutical ingredient to the total matrix composition can be 0.1:1, 0.2:1, 0.3:1, 0.4:1, 0.5:1, 0.6:1, 0.7:1, 0.8:1, 0.9:1, or 1:1. In another embodiment, the ratio of the active pharmaceutical ingredient to the total matrix composition ranges from about 0.2:1 to about 0.5:1, including all iterations of ratios within the specified range. In another embodiment, the ratio of the active pharmaceutical ingredient to the total matrix composition ranges from about 0.2:1 to about 0.4:1, including all iterations of ratios within the specified range. In one aspect, the ratio of the active pharmaceutical ingredient to the total matrix composition is about 0.3:1. In one aspect, the ratio of the active pharmaceutical ingredient to the total matrix composition is about 0.4:1. In one aspect, the ratio of the active pharmaceutical ingredient to the total matrix composition is about 0.5:1.

In one embodiment, the matrix contains an active pharmaceutical ingredient in a suspended, form, soluble form, insoluble form, or combinations thereof. In another embodiment, the matrix contains an active pharmaceutical ingredient useful for the treatment of pain. In one embodiment, the active pharmaceutical ingredient includes tapentadol, oxycodone, morphine, morphine analogues, or morphine antagonists, codeine, morphine, methadone, fentanyl and analogs, opioid pain relievers: oxycodone hydrochloride, hydrocodone bitartrate hydromorphone, oxymorphone, meperidine, propoxyphene, flunitrazepam, barbiturates, amytal, nembutal, seconal, phenobarbital; benzodiazepines, zolpidem, zaleplon, eszopiclone, amphetamines, or methylphenidate.

Examples of specific active drug substances suitable for use in the pharmaceutical compositions provided herein include: anti-inflammatory and antirheumatic active drug substances, such as, for example: butylpyrazolidine, phenylbutazone, mofebutazone, oxyphenbutazone, clofezone, kebuzone, acetic acid derivatives and related substances, indometacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, oxicam, piroxicam, tenoxicam, droxicam, lornoxicam, meloxicam, methotrexate, propionic acid derivatives, ibuprofen, naproxen, ketoprofen, fenoprofen, fenbufen, benoxaprofen, suprofen, pirprofen, flurbiprofen, indoprofen, tiaprofenic acid, oxaprozin, ibuproxam, dexibuprofen, flunoxaprofen, alminoprofen, dexketoprofen, fenamates, mefenamic acid, tolfenamic acid, flufenamic acid, meclofenamic acid, coxibs, celecoxib, rofecoxib, valdecoxib, parecoxib, etoricoxib, lumiracoxib, nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate, feprazone, dipyrocetyl, acetylsalicylic acid, quinolines, oxycinchophen, gold preparations, sodium aurothiomalate, sodium aurotiosulfate, auranofin, aurothioglucose, aurotioprol, penicillamine or bucillamine.

In another embodiment, suitable active pharmaceutical ingredients can comprise analgesics, such as, for example: opioids, natural opium alkaloids, morphine, opium, hydromorphone, nicomorphine, oxycodone, dihydrocodeine, diamorphine, tapentadol, papavereturn, codeine, phenylpiperidine derivatives, ketobemidone, pethidine, fentanyl, diphenylpropylamine derivatives, dextromoramide, piritramide, dextropropoxyphene, bezitramide, methadone, benzomorphan derivatives, pentazocine, phenazocine, oripavine derivatives, buprenorphine, morphinan derivatives, butorphanol, nalbuphine, tilidine, tramadol, dezocine, salicylic acid and derivatives, acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, pyrazolones, phenazone, metamizole sodium, aminophenazone, propyphenazone, nifenazone, anilides, paracetamol, phenacetin, bucetin, propacetamol, other analgesics and antipyretics, such as, for example: rimazolium, glafenine, floctafenine, viminol, nefopam, flupirtine, or ziconotide.

In another embodiment, suitable active pharmaceutical ingredients can comprise anaesthetics, such as, for example: ethers, diethyl ether, vinyl ether, halogenated hydrocarbons, halothane, chloroform, methoxyflurane, enflurane, trichloroethylene, isoflurane, desflurane, sevoflurane, barbiturates, methohexital, hexobarbital, thiopental, narcobarbital, opioid anaesthetics, fentanyl, alfentanil, sufentanil, phenoperidine, anileridine, remifentanil, other general anaesthetics, such as, for example: droperidol, ketamine, propanidid, alfaxalone, etomidate, propofol, hydroxybutyric acid, nitrous oxide, esketamine, xenon, esters of aminobenzoic acid, metabutethamine, procaine, tetracaine, chloroprocaine, benzocaine, amides, bupivacaine, lidocaine, mepivacaine, prilocaine, butanilicaine, cinchocaine, etidocaine, articaine, ropivacaine, levobupivacaine, esters of benzoic acid, cocaine, other local anaesthetics, such as, for example: ethyl chloride, dyclonine, phenol, or capsaicin.

In another embodiment, suitable active pharmaceutical ingredients can comprise antimigraine active drug substances, such as, for example: ergot alkaloids, dihydroergotamine, ergotamine, methysergide, lisuride, corticosteroid derivatives, flumedroxone, selective serotonin (5HT$^1$) agonists, sumatriptan, naratriptan, zolmitriptan, rizatriptan, almotriptan, eletriptan, frovatriptan, other antimigraine preparations, pizotifen, clonidine, iprazochrome, dimetotiazine, or oxetorone.

In another embodiment, suitable active pharmaceutical ingredients can comprise antiepileptic active drug substances, such as, for example: barbiturates and derivatives, methylphenobarbital, phenobarbital, primidone, barbexaclone, metharbital, hydantoin derivatives, ethotoin, phenytoin, amino(diphenylhydantoin) valeric acid, mephenytoin, fosphenytoin, oxazolidine derivatives, paramethadione, trimethadione, ethadione, succinimide derivatives, ethosuximide, phensuximide, mesuximide, benzodiazepine derivatives, clonazepam, carboxamide derivatives, carbamazepine, oxcarbazepine, rufinamide, fatty acid derivatives, valproic acid, valpromide, aminobutyric acid, vigabatrin, progabide, tiagabine, other antiepileptics, such as, for example: sultiame, phenacemide, lamotrigine, felbamate, topiramate, gabapentin, pheneturide, levetiracetam, zonisamide, pregabalin, stiripentol, lacosamide, or beclamide.

In another embodiment, suitable active pharmaceutical ingredients can comprise anticholinergic active drug substances, such as, for example: tertiary amines, trihexyphenidyl, biperiden, metixene, procyclidine, profenamine, dexetimide, phenglutarimide, mazaticol, bornaprine, tropatepine, ethers chemically close to antihistamines, etanautine, orphenadrine (chloride), ethers of tropine or tropine derivatives, benzatropine, or etybenzatropine.

In another embodiment, suitable active pharmaceutical ingredients can comprise dopaminergic active drug substances, such as, for example: dopa and dopa derivatives, levodopa, melevodopa, etilevodopa, adamantane derivatives, amantadine, dopamine agonists, bromocriptine, pergolide, dihydroergocryptine mesylate, ropinirole, pramipexole, cabergoline, apomorphine, piribedil, rotigotine, monoamine, oxidase B inhibitors, selegiline, rasagiline, other dopaminergic agents, such as, for example: tolcapone, entacapone, or budipine.

In another embodiment, suitable active pharmaceutical ingredients can comprise antipsychotic active drug substances, such as, for example: phenothiazines with aliphatic side-chain, chlorpromazine, levomepromazine, promazine, acepromazine, triflupromazine, cyamemazine, chlorproethazine, phenothiazines with piperazine structure, dixyrazine, fluphenazine, perphenazine, prochlorperazine, thiopropazate, trifluoperazine, acetophenazine, thioproperazine, butaperazine, perazine, phenothiazines with piperidine structure, periciazine, thioridazine, mesoridazine, pipotiazine, butyrophenone derivatives, haloperidol, trifluperidol, melperone, moperone, pipamperone, bromperidol, benperidol, droperidol, fluanisone, indole derivatives, oxypertine, molindone, sertindole, ziprasidone, thioxanthene derivatives, flupentixol, clopenthixol, chlorprothixene, tiotixene, zuclopenthixol, diphenylbutylpiperidine derivatives, fluspirilene, pimozide, penfluridol, diazepines, oxazepines, thiazepines, loxapine, clozapine, olanzapine, quetiapine, neuroleptics, tetrabenazine, benzamides, sulpiride, sultopride, tiapride, remoxipride, amisulpride, veralipride, levosulpiride, lithium, other antipsychotics, such as, for example prothipendyl, risperidone, clotiapine, mosapramine, zotepine, aripiprazole, or paliperidone.

In another embodiment, suitable active pharmaceutical ingredients can comprise anxiolytic active drug substances, such as, for example: benzodiazepine derivatives, diazepam, chlordiazepoxide, medazepam, oxazepam, potassium clorazepate, lorazepam, adinazolam, bromazepam, clobazam, ketazolam, prazepam, alprazolam, halazepam, pinazepam, camazepam, nordazepam, fludiazepam, ethyl loflazepate, etizolam, clotiazepam, cloxazolam, tofisopam, diphenylmethane derivatives, hydroxyzine, captodiame, carbamates, meprobamate, emylcamate, mebutamate, dibenzo-bicyclo-octadiene derivatives, benzoctamine, azaspirodecanedione derivatives, buspirone, other anxiolytics, such as, for example: mephenoxalone, gedocarnil, or etifoxine.

In another embodiment, suitable active pharmaceutical ingredients can comprise hypnotic and sedative active drug substances, such as, for example: barbiturates, pentobarbital, amobarbital, butobarbital, barbital, aprobarbital, secobarbital, talbutal, vinylbital, vinbarbital, cyclobarbital, heptabarbital, reposal, methohexital, hexobarbital, thiopental, ethallobarbital, allobarbital, proxibarbal, aldehydes and derivatives, chloral hydrate, chloralodol, acetylglycinamide chloral hydrate, dichloralphenazone, paraldehyde, benzodiazepine emepronium derivatives, flurazepam, nitrazepam, flunitrazepam, estazolam, triazolam, lormetazepam, temazepam, midazolam, brotizolam, quazepam, loprazolam, doxefazepam, cinolazepam, piperidinedione derivatives, glutethimide, methyprylon, pyrithyldione, benzodiazepine related drugs, zopiclone, zolpidem, zaleplon, ramelteon, other hypnotics and sedatives, such as, for example: methaqualone, clomethiazole, bromisoval, carbromal, scopolamine, propiomazine, triclofos, ethchlorvynol, valerian, hexapropymate, bromides, apronal, valnoctamide, methylpentynol, niaprazine, melatonin, dexmedetomidine, or dipiperonylaminoethanol.

In another embodiment, suitable active pharmaceutical ingredients can comprise antidepressant active drug substances, such as, for example: non-selective monoamine reuptake inhibitors, desipramine, imipramine, imipramine oxide, clomipramine, opipramol, trimipramine, lofepramine, dibenzepin, amitriptyline, nortriptyline, protriptyline, doxepin, iprindole, melitracen, butriptyline, dosulepin, amoxapine, dimetacrine, amineptine, maprotiline, quinupramine, selective serotonin reuptake inhibitors, zimeldine, fluoxetine, citalopram, paroxetine, sertraline, alaproclate, fluvoxamine, etoperidone, escitalopram, monoamine oxidase inhibitors, isocarboxazid, nialamide, phenelzine, tranylcypromine, iproniazide, iproclozide, monoamine oxidase A inhibitors, moclobemide, toloxatone, other antidepressants, such as, for example: oxitriptan, tryptophan, mianserin, nomifensine, trazodone, nefazodone, minaprine, bifemelane, viloxazine, oxaflozane, mirtazapine, medifoxamine, tianeptine, pivagabine, venlafaxine, milnacipran, reboxetine, gepirone, duloxetine, agomelatine, desvenlafaxine, centrally acting sympathomimetics, such as, for example: amfetamine, dexamfetamine, lisdexamfetamine, metamfetamine, methylphenidate, dexmethylphenidate, pemoline, fencamfamin, modafinil, fenozolone, atomoxetine, fenetylline, xanthine derivatives, caffeine, propentofylline, other psychostimulants and nootropics, such as, for example meclofenoxate, pyritinol, piracetam, deanol, fipexide, citicoline, oxiracetam, pirisudanol, linopirdine, nizofenone, aniracetam, acetylcarnitine, idebenone, prolintane, pipradrol, pramiracetam, adrafinil, or vinpocetine.

In another embodiment, suitable active pharmaceutical ingredients can comprise anti-dementia active drug substances, such as, for example: anticholinesterases, tacrine, donepezil, rivastigmine, galantamine, other anti-dementia drugs, memantine, or ginkgo biloba.

In another embodiment, suitable active pharmaceutical ingredients can comprise other nervous system active drug substances, such as, for example: parasympathomimetics, anticholinesterases, neostigmine, pyridostigmine, distigmine, ambenonium, choline esters, carbachol, bethanechol, and other parasympathomimetics, such as, for example, pilocarpine, or choline alfoscerate.

Active drug substances used in addictive disorders, such as, for example: nicotine, bupropion, varenicline, disulfiram, calcium carbimide, acamprosate, naltrexone, buprenorphine, methadone, levacetylmethadol, lofexidine, betahistine, cinnarizine, flunarizine, acetylleucine, gangliosides and ganglioside derivatives, tirilazad, riluzole, xaliproden, hydroxybutyric acid, or amifampridine.

In another embodiment, suitable active pharmaceutical ingredients can comprise opium alkaloids and derivatives, such as, for example: ethylmorphine, hydrocodone, codeine, opium alkaloids with morphine, normethadone, noscapine, pholcodine, dextromethorphan, thebacon, dimemorfan, acetyldihydrocodeine, benzonatate, benproperine, clobutinol, isoaminile, pentoxyverine, oxolamine, oxeladin, clofedanol, pipazetate, bibenzonium bromide, butamirate, fedrilate, zipeprol, dibunate, droxypropine, prenoxdiazine, dropropizine, cloperastine, meprotixol, piperidione, tipepidine, morclofone, nepinalone, levodropropizine, or dimethoxanate.

In another embodiment, the active pharmaceutical ingredient may be a substance with abuse potential that presents a safety risk. Such active drug substance may include: 1-(1-phenylcyclohexyl)pyrrolidine, 1-(2-phenylethyl)-4-phenyl-4-acetoxypiperidine, 1-[1-(2-thienyl)-cyclohexylpiperidine, 1-[1-(2-thienyl)cyclohexyl]pyrrolidine, 1-methyl-4-phenyl-4-propionoxy-piperidine, 1-phenylcyclohexylamine, 1-piperidinocyclohexanecarbonitrile, 2,5-dimethoxy-4-ethylamphetamine, 2,5-dimethoxyamphetamine, 2C—B-(4-bromo-2,5-dimethoxypenethylamine), 2C-D (2,5-dimethoxy-4-methylphenethylamine), 2C—I (4-iodo-2,5-dimethoxyphenethylamine), 2C-T-2 (2,5-dimethoxy-4-ethylthiophenethylamine), 2C-T-4 (2,5-dimethoxy-4-isopropyl thiophenethylamine), 2C-T-7 (2,5-dimethoxy-4-(n)-propylthiophenethylamine), 3,4-methylenedioxymethamphetamine, 3,4,5-trimethoxyamphetamine, 3,4-methylenedioxyamphetamine, 3,4-methylenedioxy-N-ethylamphetamine, 3-methylfentanyl, 3-methylthiofentanyl, 4-brorno-2,5-dimethoxyamphetamine, 4-bromo-2,5-dimethoxyphenethylamine, 4-methoxyamphetamine, 4-methyl-2,5-dimethoxyamphetamine, 4-methylaminorex (cis isomer), 5-MeO-DIPT (5-methoxy-N,N-diisopropyltryptamine), 5-MeO-DMT (5-methoxy-N,N-dimethyltryptamine), 5-methoxy-3,4-methylenedioxyamphetamine, acetorphine, acetorphine, acetyl-alpha-methylfentanyl, acetyl-alpha-methylfentanyl, acetyldihydrocodeine, acetylmethadol, acetylmethadol, alfentanil, allobarbital, allylprodine, alphacetylmethadol except levo-alphacetylmethadol, alpha-ethyltryptamine, alphameprodine, alphamethadol, alphamethadol, alpha-methylfentanyl, alpha-methylthiofentanyl, alphaprodine, alprazolam, amfepramon, amfetaminil, amineptin, aminorex, amobarbital, amphetamine, dextroamphetamine, amilnitrite (all isomers of the amyl group), anabolic steroids, anileridine, aprobarbital, barbital, barbituric acid derivative, BDB (3,4-methylenedioxyphenyl)-2-butanamine), benzethidin, benzethidine, benzoylecgonine, benzphetamine, benzphetamine, benzylmethylcetone, benzylmorphine, betacetylmethadol, beta-hydroxy-3-methylfentanyl, beta-hydroxyfentanyl, betameprodine, betameprodine, betamethadol, betaprodine, bezitramide, bezitramide, boldenone, brolamfetamine, bromazepam, brotizolam, bufotenine, buprenorphine, butabarbital, butalbital, butobarbital, butorphanol, BZP (A2)(1-benzylpiperazin), camazepam, cannabis, carfentanil, catha edulis, cathine, cathinone, chloral betaine, chloral hydrate, chlordiazepoxide, chlorhexadol, chlorotestosterone (same as clostebol), chlorphentermine, clobazam, clonazepam, clonitazene, clonitazene, clorazepate, clortermine, clostebol, clotiazepam, cloxazolam, coca leaves, cocaine, codeine, codeine and isoquinoline alkaloid, codeine methylbromide, codeine-N-oxide, codoxime, cyclobarbital (hexemal NFN), cyprenorphine, dehydrochlormethyltestosterone, delorazepam, desomorphine, dexamfetamine, dexfenfluramine, dexmethylphenidate, dextromoramide, dextropropoxyphene, diacetylmorphine, diampromide, diazepam, dichloralphenazone, diethylpropion, diethylthiambutene, diethyltryptamine, difenoxin, dihydrocodeine, dihydroetorphine, dihydromorphine, dihydrotestosterone, dimenoxadol, dimepheptanol, dimethylthiambutene, dimethyltryptamine, dioxaphetyl butyrate, diphenoxylate, dipipanone, diprenorphine, dronabinol, drostanolone, drotebanol, ecgonine, estazolam, ethchlorvynol, ethinamate, ethyl loflazepate, ethylestrenol, ethylmethylthiambutene, ethylmorphine, ethylmorphine, eticyclidine, etilamfetamine, etonitazene, etorphine, etoxeridine, etryptamine, fencamfamin, fenethylline, fenetylline, fenfluramine, fenproporex, fentanyl, fludiazepam, flunitrazepam, fluoxymesterone, flurazepam, formebolone, fungi and spores of the species psilocybe semilanceata, furethidine, gamma hydroxybutyric acid, glutethimide, halazepam, haloxazolam, heroine, hydrocodone, hydrocodone & isoquinoline alkaloid, hydromorphinol, hydromorphone, hydroxypethidine, ibogaine, isobutyl nitrite, isomethadone, ketamine, ketazolam, ketobemidone, levamfetamine, levo-alphacetylmethadol, levo-methamphetamine, levomethorphan, levomoramide, levophenacylmorphan, levorphanol, lisdexamfetamine, loprazolam, lorazepam, lormetazepam, lysergic acid, lysergic acid amide, lysergic acid diethylamide, marijuana, mazindol, MBDN (N-methyl-1-(3,4-methylenedioxyphenyl)-2-butanamine), mCPP (1-(3-chlorphenyl)piperazine), mebutamate, mecloqualone, medazepam, mefenorex, MeOPP (1-(4-methoxyphenyl)piperazine), meperidine, meperidine intermediate, meprobamate, mescaline, mesocarb, mesterolone, metamfetamine, metazocine, methadone, methadone intermediate, methamphetamine, methandienone, methandrolone, methandriol, methandrostenolone, methaqualone, methcathinone, methenolone, methohexital, methyldesorphine, methyldihydromorphine, methylphenidate, methylphenobarbital (mephobarbital), methyltestosterone, methyprylone, metopone, mibolerone, midazolam, modafinil, moramide-intermediate, morpheridine, morphine, morphine methylbromide, morphine methylsulfonate, morphine-N-oxide, myrophine, N,N-dimethylamphetamine, nabilone, nalorphine, nandrolone, N-ethyl-1-phenylcyclohexylamine, N-ethyl-3-piperidyl benzilate, N-ethylamphetamine, N-hydroxy-3,4-methylenedioxyamphetamine, nicocodeine, nicocodine, nicodicodine, nicomorphine, nimetazepam, nitrazepam, N-methyl-3-piperidyl benzilate, noracymethadol, norcodeine, nordiazepam, norethandrolone, norlevorphanol, normethadone, normorphine, norpipanone, norpipanone, opium, oxandrolone, oxazepam, oxazolam, oxycodone, oxymesterone, oxymetholone, oxymorphone, para-fluorofentanyl, parahexyl, paraldehyde, pemoline, pentazocine, pentobarbital, petrichloral, peyote, phenadoxone, phenampromide, phenazocine, phencyclidine, phendimetrazine, phenmetrazine, phenobarbital, phenomorphan, phenoperidine, phentermine, phenylacetone, pholcodine, piminodine, pinazepam, pipradrole, piritramide, PMMA (paramethyxymethyl amphetamine), prazepam, proheptazine, properidine, propiram, psilocybine, psilocine, pyrovalerone, quazepam, racemethorphane, racemoramide, racemorphane, remifentanil, salvia divinorum, salvinorin A, secobarbital, secobarbital, sibutramine, SPA, stanolone, stanozolol, sufentanil, sulfondiethylmethane, sulfonethylmethane, sulfonmethane, talbutal, temazepam, tenamfetamine, testolactone, testosterone, tetrahydrocannabinols, tetrazepam, TFMPP (1-(3-triflourmethylphenyl)piperazine), thebacon, thebaine, thiamylal, thiofentanyl, thiopental, tiletamine and zolazepam in combination, tilidine, trenbolone, triazolam, trimeperidine, vinbarbital, zaleplon, zipeprol, zolpidem, or zopiclone.

Other suitable examples of active drug substances suitable for use in the pharmaceutical compositions described herein include, for example, alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, morphine 6-glucuronide, morphine 3-glucuronide, myrophine, nalbuphine, narcine, nicomorphine, norlevorphanol, normethadone, nalorphine, normorphine, norpipanone, opium, oxycodone, oxycodeine, oxymorphone, papavereturn, pentazocine, phenadoxone, phenomorphan, phenazocine, phenoperidine, piminodine, piritramide, propheptazine, promedol, properidine, propiram, propoxyphene, sufentanil, tilidine, tramadol, thebaine, levo-alphacetylmethadol (LAAM), remifentanil, carfentanyl, ohmefentanyl, MPPP, prodine, PEPAP, levomethorphan, etorphine, lefetamine, loperamide, diphenoxylate, or pethidine.

Other examples of active drug substances suitable for use in the pharmaceutical compositions described herein include anabolic steroids, cannabis, cocaine, or diazepam.

In another embodiment, the active drug substance comprises the therapeutic classes including non-steroidal anti-inflammatory substances or antirheumatic active drug substances.

In other embodiments, the active drug substance comprises analgesics, opioids, antipyretics, anaesthetics, antimigraine agents, antiepileptics, anti-parkinson agents, dopaminergic agents, antipsychotics, anxiolytics, sedatives, antidepressants, psychostimulants agents, dopamine, noradrenaline, nicotinic, alfa-adrenergic, serotonin, H3 antagonists used for ADHD or nootropics agents used in addictive disorders.

In other embodiments, the active drug substance comprises therapeutic classes including anaesthetics, centrally acting analgesics, sedative-hypnotics, anxiolytics, appetite suppressants, decongestants, antitussives, antihistamines, antiemetics, antidiarrheals, and drugs used to treat narcolepsy, or attention deficit hyperactivity disorder.

In another embodiment, the active drug substance is associated with abuse syndromes and the active drug substance may, for example, be selected from opioids, CNS depressants, CNS stimulants, cannabinoids, nicotine-like compounds, glutamate antagonists, or N-methyl-D-aspartate (NMDA) antagonists.

In another embodiment, the active drug substance is an analgesic. Examples of analgesics suitable for use in the pharmaceutical compositions described herein include, for example, opioids, natural opium alkaloids, morphine, opium, hydromorphone, nicomorphine, oxycodone, dihydrocodeine, diamorphine, tapentadol, papavereturn, codeine, phenylpiperidine derivatives, ketobemidone, pethidine, fentanyl, diphenylpropylamine derivatives, dextromoramide, piritramide, dextropropoxyphene, bezitramide, methadone, benzomorphan derivatives, pentazocine, phenazocine, oripavine derivatives, buprenorphine, morphinan derivatives, butorphanol, nalbuphine, tilidine, tramadol, dezocine, salicylic acid and derivatives, acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, pyrazolones, phenazone, metamizole sodium, aminophenazone, propyphenazone, nifenazone, anilides, paracetamol, phenacetin, bucetin, propacetamol, other analgesics and antipyretics such as, for example, rimazolium, glafenine, floctafenine, viminol, nefopam, flupirtine, or ziconotide.

In another embodiment, the active drug substance is an opioid. Where an opioid is included as an active drug substance, the opioid may comprise naturally occurring opioids, synthetic opioids, or semisynthetic opioids.

In other embodiment, the active drug substance comprises amfetamine, dexamfetamine, lisdexamfetamine, metamfetamine, methylphenidate, dexmethylphenidate, or combinations thereof.

In another embodiment, the pharmaceutical compositions disclosed herein includes an opioid, the opioid is selected from buprenorphine, codeine, dextromoramide, dihydrocodeine, fentanyl, hydrocodone, hydromorphone, morphine, pentazocine, oxycodeine, oxycodone, oxymorphone, norhydrocodone, noroxycodone, morphine-6-glucuronode, tramadol, tapentadol, or dihydromorphine.

Where an opioid is used as an active drug substance, the opioid may be present in any of its crystalline, polymorphous, semi-crystalline, and amorphous or polyamorphous forms. Furthermore, in another embodiment, an opioid used as an active drug substance may be present in one or more forms selected from its crystalline, polymorphous, semi-crystalline, or amorphous or polyamorphous forms.

Some embodiments of the pharmaceutical compositions disclosed herein include an opioid as an active drug substance, the active drug substance is selected from morphine, oxycodone, hydrocodone, hydromorphone, norhydrocodone, oxymorphone, noroxycodone, morphine-6-glucuronode and pharmaceutically acceptable salts thereof, including oxycodone hydrochloride, hydrocodone bitartrate, hydromorphone hydrochloride or morphine sulphate pentahydrate.

In other embodiments, the pharmaceutical compositions as described herein are suitable for use for water soluble as well as slightly soluble or insoluble active drug substances.

In another embodiment, all of the above mentioned active drug substances may also be in the form of pharmaceutically acceptable salts, uncharged or charged molecules, molecular complexes, solvates, or anhydrates thereof, and, if relevant, single isomers, enantiomers, racemic mixtures, or mixtures thereof.

In another embodiment, the pharmaceutical compositions described herein may comprise pharmaceutically acceptable salts of any of the above mentioned active drug substances.

In another embodiment, the active pharmaceutical ingredient is tapentadol or a pharmaceutically acceptable salt form. Pharmaceutically acceptable salts forms are those formed by contacting tapentadol free base with a suitable acid in a suitable solvent under suitable conditions that will form a form of tapentadol acid addition salt. Suitable acids include hydrochloric acid, camphorsulfonic acid, hydrobromic acid, sulfuric acid, methanesulfonic acid, formic acid, acetic acid, oxalic acid, succinic acid, tartaric acid, mandelic acid, malic acid, salicylic acid, fumaric acid, lactic acid, citric acid, glutamic acid, and/or aspartic acid. In another embodiment, the suitable tapentadol salt may include: tapentadol hydrochloride, tapentadol L-(−)-camphorsulfonate, tapentadol dibenzoyl-(L)-tartrate, tapentadol dibenzoyl-(D)-tartrate, tapentadol malate, or tapentadol maleate.

The term "pharmaceutically acceptable salts" of an active drug substance includes alkali metal salts such as, for example, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, toluenesulphonic acid etc. In another embodiment, pharmaceutically acceptable opioid salts can comprise sulphate salts, hydrochloride salts, and bitartrate salts.

In another embodiment, the active pharmaceutical ingredient may be in any of its crystalline, polymorphous, semicrystalline, amorphous or polyamorphous forms or mixtures thereof.

The concentration of the active drug substance in the pharmaceutical composition for use according to the disclosure depends on the specific active drug substance, the disease to be treated, the condition of the patient, the age, and gender of the patient, etc. The above-mentioned active drug substances may be known active drug substances and a person skilled in the art will be able to find information as to the dosage of each active drug substance and, accordingly, will know how to determine the amount of each active drug substance in the pharmaceutical composition.

The active pharmaceutical ingredient may be a new chemical entity for which the amount of information is limited. In such cases, the dosage has to be evaluated based on available preclinical and/or clinical data.

In one embodiment described herein, the pharmaceutical composition comprises soft capsule shell comprising a matrix comprising an active pharmaceutical ingredient.

In one embodiment described herein, the soft capsule shell has the composition of Table 2, including all possible iterations of the specified ranges that provide 100% for the total weight percentage, including or excluding the optional colorings, flavorings, or excipients.

TABLE 2

Exemplary soft gelatin capsule composition

| Component | Exemplary Component | Weight Percentage (%) |
|---|---|---|
| Film-forming polymer | Gelatin | 25-50 |
| Plasticizer | Glycerol | 15-25 |
| Solvent | Water | 20-40 |
| Opacifier (optional) | Titanium dioxide | 0.5-1.5 |
| Coloring agent (optional) | Various | 0.05-0.1 |
| TOTAL | | 100% |

Film-former polymers that are useful for creating soft capsules as described herein are gelatin or hydroxypropylmethylcellulose (HPMC). In one aspect, the film-forming polymer is gelatin.

Plasticizers that are useful for creating soft capsules as described herein are glycerol, sorbitol, polyethylene glycols, or combinations thereof. The weight ratio between the film-forming polymer, plasticizer, and solvent is adjusted so that the gel mass is flowable and not too viscous, and can be made into soft capsules using rotary die encapsulation methods.

In one embodiment, the enteric soft capsule shell has the exemplary composition shown in Table 3.

TABLE 3

Exemplary Soft Capsule Shell Composition

| Component | Percent weight (%) |
|---|---|
| Gelatin | 43 |
| Glycerol | 20 |
| Titanium dioxide (optional) | 0.7 |
| Coloring agent (optional) | 0.1 |
| Water | 36.2 |
| TOTAL | 100% |
| Final pH | ~4-7 |
| Ratio total plasticizer to gelatin | 20:43 (0.46:1) |
| Water content in dried soft capsule shell: | 8-15% |

In one embodiment described herein, the soft capsule comprises about 43% of at least one film-forming polymer; about 20% of at least one plasticizer; about 36% water; optionally, about 0.7% titanium dioxide; and optionally, about 0.1% of at least one coloring agent.

In one embodiment, the weight percentage range of film-forming polymer of the soft capsule described herein is about 35% to about 45%, including all integers within the specified range. In one aspect, the film-forming polymer weight percentage is about 38%. In another aspect, the film-forming 1 polymer weight percentage is about 42%. In another aspect, the film-forming polymer weight percentage is about 44%.

In one embodiment, the weight percentage range of plasticizer is about 15% to about 22%, including all iterations of integers with the specified range. In one aspect, the plasticizer weight percentage is about 17%. In another aspect, the plasticizer weight percentage is about 18.5%. In another aspect, the plasticizer weight percentage is about 20%.

In one embodiment, the weight percentage ratio range of plasticizer to film-forming polymer is about 0.33:1 to about 0.56:1, including all iterations of iterations of ratios with the specified range. In one embodiment, the weight percentage ratio range of plasticizer to film-forming polymer is about 0.38:1. In one embodiment, the weight percentage ratio range of plasticizer to film-forming polymer is about 0.42:1. In one embodiment, the weight percentage ratio range of plasticizer to film-forming polymer is about 0.46:1. In one embodiment, the weight percentage ratio range of plasticizer to film-forming polymer is about 0.52:1.

In one aspect, soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing soft capsules comprising the pharmaceutical composition as described herein. The process includes preparing a gel mass composition comprising a film-forming, water-soluble polymer, an appropriate plasticizer, and solvent; casting the gel mass into films or ribbons using heat-controlled drums or surfaces; and manufacturing a soft capsule comprising a matrix fill using rotary die technology. The thickness of the films or ribbons that form the soft capsule shell is from about 0.010 inches (≈0.254 mm) to about 0.050 inches (≈21.27 mm), including all integers within the specified range. The shell thickness can be about 0.010 inch (≈0.254 mm), about 0.015 inch (≈0.381 mm), about 0.02 in (≈0.508 mm), about 0.03 in (≈0.762 mm), about 0.04 in (≈21.02 mm), or about 0.05 in (≈1.27 mm). In one embodiment, the thickness is about 0.02 inches (≈0.508 mm) to about 0.040 inches (≈21.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm).

In one embodiment described herein, the soft capsule shell described herein, encapsulates a matrix fill as described herein. In another embodiment described herein, the soft capsule shell and encapsulated matrix fill comprises a outer dimension from about 2 oval to about 30 oval including all iterations of capsule size within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the soft capsule shell and encapsulated matrix fill comprises a outer dimension from about 2 round to about 28 round including all iterations of capsule size within the specified range (e.g., 2 round, 3 round, 4 round, 5 round, 6 round, 7 round, 8 round, 10 round, 12 round, 16 round, 20 round or 28 round). In another embodiment described herein, the soft capsule shell and encapsulated matrix fill comprises a outer dimension from about 2 oblong to about 22 oblong including all iterations of capsule size within the specified range (e.g., 2 oblong, 3 oblong, 4 oblong, 5 oblong, 6 oblong, 7 oblong, 8 oblong, 10 oblong, 11 oblong, 12 oblong, 14 oblong, 16 oblong, 20 oblong, or 22 oblong). Dimension specifications of soft capsules and tablets are known to those skilled in the art. See *Remington's Essentials of Pharmaceutics*, Pharmaceutical Press Publishing Company, London, UK, 1$^{st}$ Edition, 2013, which is incorporated by reference herein for such teachings.

In another embodiment described herein, the pharmaceutical composition comprises an enteric soft capsule shell comprising a matrix fill comprising an active pharmaceutical ingredient.

Enteric soft capsules are described in International Patent Application Publication No. WO 2004/030658; U.S. Patent Application Publication No. US 2006/0165778; and U.S. Pat. No. 8,685,445, each of which is incorporated by reference herein for such teachings. The enteric soft capsule shell may comprise one or more film forming polymers, one or more enteric acid-insoluble polymers, one or more plasticizers, one or more alkali-neutralizing agents, one or more solvents, optionally one or more colorants, and optionally one or more flavorings or other conventionally accepted pharmaceutical excipients or additives.

Film-former polymers that are useful for creating enteric soft capsules are gelatin or hydroxypropylmethylcellulose (HPMC). In one aspect of the enteric soft capsule shell described herein, the film-forming polymer is gelatin.

Examples of enteric, acid-insoluble polymers are acrylic and methacrylate acid copolymers, cellulose acetate phthalate (CAP), cellulose acetate butyrate, hydroxypropylmethylcellulose phthalate (HPMCP), algenic acid salts such as sodium or potassium alginate, or shellac. Poly(methacylic acid-co-methyl methacrylate) anionic copolymers based on methacrylic acid and methyl methacrylate are particularly stable and are preferred in some embodiments. Poly(meth) acrylates (methacrylic acid copolymer), available under the trade name EUDRAGIT® (Evonik Industries AG, Essen, Germany), are provided as powder or aqueous dispersions. In one aspect, the methacrylic acid copolymer can be EUDRAGIT® L 30 D-55; EUDRAGIT® L 100-55; EUDRAGIT® L 100; EUDRAGIT® L 12.5; EUDRAGIT® S 100; EUDRAGIT® S 12.5; EUDRAGIT® FS 30 D; EUDRAGIT® E 100; EUDRAGIT® E 12.5; EUDRAGIT® E PO; EUDRAGIT® RL 100; EUDRAGIT® RL PO; EUDRAGIT® RL 30 D; EUDRAGIT® RL 12.5; EUDRAGIT® RS 100; EUDRAGIT® RS PO; EUDRAGIT® RS 30 D; EUDRAGIT® RS 12.5; EUDRAGIT® NE 30 D; EUDRAGIT® NE 40 D; EUDRAGIT® NM 30 D; or other poly(meth)acrylate polymers. In one aspect, the enteric polymer is EUDRAGIT® L 100, a methacrylic acid copolymer, Type A. Acid-insoluble polymer specifications are detailed in the United States Pharmacopoeia and in various monographs.

Plasticizers that are useful for creating enteric soft capsules as described herein are glycerol, sorbitol, polyethylene glycol, citric acid, citric acid esters, such as tri-ethyl citrate, or combinations thereof. The weight ratio between the film-forming polymer, the enteric acid-insoluble polymer, and plasticizer is adjusted so that the gel mass is flowable and not too viscous, and can be made into soft capsules using rotary die encapsulation methods.

In one embodiment, enteric soft capsule shell compositions can be made by dissolving the enteric acid-insoluble polymer in an aqueous solution of an alkali neutralizing agent such as ammonia, sodium hydroxide, potassium hydroxide, or liquid amines such as tri-ethanol amine or ethylene diamine. The amount of alkali is adjusted to give a final pH value of the gel mass less than or equal to about pH 9.0. In one embodiment, the final pH does not exceed 8.5. The volatile alkali neutralizing agent, ammonia is preferred. The film-forming polymer can then be combined with the plasticizer and solvent and then blended with the acid-insoluble gel to make a final homogeneous mix in a heat-controlled vessel and can be degassed by using vacuum. The fugitive ammonia evaporates during degassing. Using the foregoing process, the alkali concentrations do not require an additional step such as heating or neutralizing with acid in order to neutralize the gel mass.

In another embodiment described herein, an enteric soft capsule shell can be made by using an aqueous dispersion of the acid-insoluble polymer by adding alkaline materials such as ammonium, sodium, or potassium hydroxides, other alkalis, or a combination thereof that will cause the enteric acid-insoluble polymer to dissolve. The plasticizer-wetted, film-forming polymer can then be mixed with the solution of the acid-insoluble polymer. In one embodiment, enteric acid-insoluble polymers in the form of salts of the above-mentioned bases or alkalis can be dissolved directly in water and mixed with the plasticizer-wetted, film-forming polymer.

In one embodiment, an enteric soft capsule shell has the composition of Table 4, including all possible iterations of the specified ranges that provide 100% for the total weight percentage, including or excluding the optional, excipients, opacifiers, colorants, and flavorings.

TABLE 4

Exemplary Enteric Soft Capsule Shell Composition

| Component | Exemplary Component | Composition Range (%) |
|---|---|---|
| Film-forming polymer | Gelatin | 20-36 |
| Enteric, acid insoluble polymer | Methacrylic Acid Copolymer | 8-20 |
| Plasticizer | Glycerol, Triethyl citrate | 15-22 |
| Alkali neutralizing agents | NH$_4$OH (30%), NaOH | 1-5 |
| Solvent | Water | 20-40 |
| Opacifier | Titanium Dioxide | 1-7.5 |
| Colorant (optional) | Various | 0.05-1 |
| Flavoring (optional) | Various | 0.05-2 |
| Excipients (optional) | Various | 1-5 |

In one embodiment, an enteric soft capsule shell comprises a composition of about 30% film forming polymer;

about 10% enteric, acid insoluble polymer; about 20% plasticizer; about 1% alkali neutralizing agent; and about 37% solvent.

In one embodiment, the weight percentage range of total polymer content (i.e., film forming polymer and enteric acid-insoluble polymer) of the enteric soft capsule described herein is about 30% to about 45%, including all integers within the specified range. In one aspect, the total polymer weight percentage is about 40%. In another aspect, the total polymer weight percentage is about 42%. In another aspect, the total polymer weight percentage is about 45%. In another aspect, the total polymer weight percentage is about 38%.

In one embodiment, the weight percentage range of total plasticizer is about 15% to about 22%, including all iterations of integers with the specified range. In one aspect, the total plasticizer weight percentage is about 19%. In another aspect, the total plasticizer weight percentage is about 17.7%. In another aspect, the total plasticizer weight percentage is about 18.9%. In another aspect, the total plasticizer weight percentage is about 19.3%.

In one embodiment, the alkali neutralizing-agent is ammonia (ammonium hydroxide; 30% w/v) that is added to comprise a weight percentage of about 1 to about 5% of the total enteric soft capsule composition. In one aspect, 30% w/v ammonia is added to comprise a weight percentage of about 2%. In another aspect, 30% w/v ammonia is added to a weight percentage of about 1.7%. In one aspect, ammonia is added to provide a final pH of about 9 in the enteric soft capsule composition. In another aspect, ammonia is added to provide a final pH of about 8.5 in the enteric soft capsule composition. In another aspect, after the capsules are filled and dried, the ammonia concentration is substantially reduced, owing to the fugitive nature of the volatile alkali. In one aspect, practically all of the ammonia is evaporated except for ammonium ions comprising salts with other moieties in the composition.

In one embodiment, the weight ratio range of film forming polymer to enteric acid insoluble polymer (film forming:enteric) is about 25:75 (≈0.33) to about 40:60 (≈0.67) (i.e., ≈0.33-0.67), including all iterations of ratios within the specified range. In one aspect, the ratio of film forming polymer to enteric acid insoluble polymer is about 30:70 (≈0.43). In another aspect, the ratio of film forming polymer to enteric acid insoluble polymer is about 28:72 (≈0.38).

In one embodiment, the weight ratio of total plasticizer to film forming polymer is about 20:40 to 21:30 (i.e., ≈4.5-0.7), including all iterations of ratios within the specified range. In one aspect, the weight ratio of total plasticizer to film forming polymer is about 20:40 (≈4.5). In another aspect, the weight ratio of total plasticizer to film forming polymer is about 21:30 (≈4.7). In another aspect, the weight ratio of total plasticizer to film forming polymer is about 19:29 (≈0.65). In another aspect, the weight ratio of total plasticizer to film forming polymer is about 19.3:29.2 (≈0.66).

In one embodiment, the weight ratio of total plasticizer to enteric acid insoluble polymer is about 1:1 to about 2:1 (≈1-2), including all iterations of ratios within the specified range. In one aspect, the weight ratio of total plasticizer to enteric acid insoluble polymer is about 11:10 (≈1.1). In another aspect, the weight ratio of total plasticizer to enteric acid insoluble polymer is about 14:10 (≈1.4). In another aspect, the weight ratio of total plasticizer to enteric acid insoluble polymer is about 17:10 (≈1.7). In another aspect, the weight ratio of total plasticizer to enteric acid insoluble polymer is about 20:10 (≈2). In another aspect, the weight ratio of total plasticizer to enteric acid insoluble polymer is about 19.3:11.2 (≈21.73).

In one embodiment, the weight ratio range of total plasticizer to total polymer (film forming and enteric acid insoluble polymer) is about 18:45 to about 20:40 (i.e., ≈4.40-0.5), including all iterations of ratios within the specified range. In one aspect, the weight ratio range of total plasticizer to total polymer is about 18:45 (≈0.40). In another aspect, the weight ratio range of total plasticizer to total polymer is about 19:40 (≈0.475). In another aspect, the weight ratio range of total plasticizer to total polymer is about 20:40 (≈0.5). In another aspect, the weight ratio range of total plasticizer to total polymer is about 19.3:40.4 (≈0.477).

In one embodiment, the solvent comprises about 20% to about 40% of the enteric soft capsule composition, including all integers within the specified range. In one embodiment, the solvent is water. The quantity of water in the composition varies depending on the quantities of the other ingredients. For example, the quantity of opacifier, colorant, flavoring, or other excipients can change the percentage of water present the composition. In one embodiment, the weight percentage of water is as much as suffices to bring the total weight percentage to 100% (i.e., quantum sufficiat; q.s.). In another embodiment, the water comprises about 20%, about 25%, about 30%, about 35%, or about 40% of the enteric soft capsule composition. In another embodiment, water comprises about 35% to about 40% of the enteric soft capsule composition. In one embodiment, water comprises about 37% of the composition.

In one embodiment, the final moisture (water) content of the enteric soft capsule is from about 8% to about 15%, including all integers within the specified range. In another embodiment, the moisture content is about 8% to about 12%, including all integers within the specified range. In one aspect, the final moisture content is about 8%. In one aspect, the final moisture content is about 9%. In one aspect, the final moisture content is about 10%. In one aspect, the final moisture content is about 11%. In another aspect, the final moisture content is about 12%.

In one embodiment, the enteric soft capsule shell has the exemplary composition shown in Table 5.

TABLE 5

Exemplary Enteric Soft Capsule Shell Composition

| Component | Percent weight |
| --- | --- |
| Gelatin | 29.2 |
| Methacrylic Acid Copolymer (EUDRAGIT ® L 100) | 11.2 |
| Glycerol | 18.0 |
| Triethyl citrate | 1.3 |
| Ammonium hydroxide | 1.7 |
| Titanium dioxide | 1.5 |
| Water | 37.1 |
| TOTAL | 100% |
| Final pH | ~4-9 |
| Total polymer % weight (gelatin + enteric) | 40.4% |
| Gelatin % wt of total polymer (gelatin + enteric) | 72.4% |
| Enteric % wt of total polymer (gelatin + enteric) | 27.6% |
| Ratio of Enteric to Gelatin | 11.2:29.2 (0.38) |
| Total plasticizer % weight (glycerol + triethyl citrate) | 19.3% |
| Ratio of total plasticizer to total polymer | 19.3:40.4 (0.48) |
| Ratio total plasticizer to gelatin | 19.3:29.2 (0.66) |
| Ratio total plasticizer to enteric | 19.3:11.2 (1.73) |
| Water content in dried enteric soft capsule: | 8-15% |

In one embodiment, the enteric soft capsule shell comprises about 30% gelatin; about 10% poly(methyl) acrylate copolymer; about 18% glycerol; about 1% triethyl citrate; about 1.5% ammonia; about 37% water; and about 1.5% titanium dioxide.

One embodiment described herein provides an enteric acid-insoluble polymer dispersed within the film-forming polymer gel mass that provides the total soft gel composition with enteric acid-insoluble properties, at relatively low concentrations of the enteric acid-insoluble polymer (e.g., from about 8% to about 20% of the total wet gel mass composition) and without the need of excessive amounts of alkali, thus avoiding denaturation or degradation of the film-forming polymer that can weaken the integrity of the enteric soft capsule shell.

In some embodiments, the enteric soft capsule shell does not dissolve or disintegrate in acids, such as 0.1N hydrochloric acid or simulated gastric fluid (ca. pH 1.2), despite the fact that the majority of the shell ingredients (i.e., greater than 50%) normally dissolve in, or are miscible with, acids. In some embodiments, the enteric soft capsules made using the compositions described herein remain intact in hydrochloric acid or simulated gastric fluid for at least two hours and the capsules readily release their contents upon shifting the pH of the solution to ca. 6.8, such as that of simulated intestinal fluid. In one aspect, the enteric soft capsule is resistant to dissolution at about pH 1.2 for at least about 2 hours. In another aspect, the enteric soft capsule begins dissolution at pH of about 6.8 within about 10 min.

In another embodiment, the final enteric capsule composition provides films of increased strength without substantially compromising film elasticity. Moreover, films made from the enteric soft capsule compositions as described herein can be sealed at normal temperature range typically used for making traditional soft gel capsules. In one aspect, enteric soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing enteric soft capsules comprising the pharmaceutical composition as described herein. The process includes preparing a gel mass composition comprising a film-forming, water-soluble polymer and an enteric acid-insoluble polymer and mixing with appropriate plasticizers and solvent; casting the gel mass into films or ribbons using heat-controlled drums or surfaces; and manufacturing a soft capsule comprising a matrix fill using rotary die technology. The thickness of the films or ribbons that form the enteric capsule shell is from about 0.010 inches (≈0.254 mm) to about 0.050 inches (≈21.27 mm), including all integers within the specified range. The shell thickness can be about 0.010 inch (≈0.254 mm), about 0.015 inch (≈0.381 mm), about 0.02 in (≈0.508 mm), about 0.03 in (≈0.762 mm), about 0.04 in (≈21.02 mm), or about 0.05 in (≈21.27 mm). In one embodiment, the thickness is about 0.02 inches (≈0.508 mm) to about 0.040 inches (≈21.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm).

In one embodiment described herein, the enteric soft capsule shell described herein, encapsulates a matrix fill as described herein. In another embodiment described herein, the enteric soft capsule shell and encapsulated matrix fill comprises a outer dimension from about 2 oval to about 30 oval including all iterations of capsule size within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the enteric soft capsule shell and encapsulated matrix fill comprises a outer dimension from about 2 round to about 28 round including all iterations of capsule size within the specified range (e.g., 2 round, 3 round, 4 round, 5 round, 6 round, 7 round, 8 round, 10 round, 12 round, 16 round, 20 round or 28 round). In another embodiment described herein, the enteric soft capsule shell and encapsulated matrix fill comprises a outer dimension from about 2 oblong to about 22 oblong including all iterations of capsule size within the specified range (e.g., 2 oblong, 3 oblong, 4 oblong, 5 oblong, 6 oblong, 7 oblong, 8 oblong, 10 oblong, 11, oblong, 12 oblong, 14 oblong, 16 oblong, 20 oblong, or 22 oblong). Dimension specifications of soft capsules and tablets are known to those skilled in the art. See *Remington's Essentials of Pharmaceutics*, Pharmaceutical Press Publishing Company, London, UK, 1$^{st}$ Edition, 2013, which is incorporated by reference herein for such teachings.

The pharmaceutical composition described herein can comprise a soft capsule comprising a matrix fill that is liquid, semi-solid, or solid. Capsules prepared as described herein can contain a hydrophobic solution or suspension, such as vegetable oils or shortening, or waxes, or combinations thereof. The matrix can be formulated to prevent interaction with the capsule shell components and release the pharmaceutical composition at a specified rate.

One embodiment described herein, is a pharmaceutical composition comprising a matrix fill formulation comprising any of the formulations shown in the Tables or Examples described herein. Any of the components of the formulations shown in the Tables or Examples can be increased, decreased, combined, recombined, switched, or removed to provide for a formulation comprising about 100% by weight.

In another embodiment, the abuse deterrent pharmaceutical composition described herein provides a dosage of an active pharmaceutical ingredient described herein for administration to a subject. The dosage form can be administered, for example, to a subject, or a subject in need thereof. In one aspect, the subject is a mammal, or a mammal in need thereof. In one aspect, the subject is a human, or human in need thereof. In one aspect, the human or human in need thereof is a medical patient. In one aspect, the human subject is a child (~0-9 years old) or an adolescent (~10-17 years old). In one aspect, the subject is from 0 to 9 years of age. In another aspect, the human subject is from 10 to 17 years of age. In another aspect, the human subject is over 17 years of age. In another aspect, the human subject is an adult (≥18 years of age).

In one embodiment, the dosage may be administered to a human in need of management of moderate to severe chronic pain and neuropathic pain associated with diabetic peripheral neuropathy (DPN), when a continuous, persistent (around-the-clock) opioid analgesic is needed for an extended period of time.

The dosage form can be administered, for example, 1×, 2×, 3×, 4×, 5×, 6×, or even more times per day. One or more dosage form can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition including but not limited to, pain.

In one embodiment, the pharmaceutical composition described herein is administered in multiple dosages simultaneously. For example, two or more identical dosages are administered at one time. In another embodiment, two or more different dosages are administered at one time. Such dual or different simultaneous doses can be used to provide an effective amount of the pharmaceutical composition to a subject in need thereof.

In one embodiment, the abuse deterrent oral composition described herein, comprises an active pharmaceutical ingredient in an amount of about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, or even more.

In another embodiment, the abuse deterrent oral composition described herein, comprises an active pharmaceutical ingredient in the range of about 20 mg to about 250 mg, about 30 mg to about 250 mg, about 40 mg to about 250 mg, about 50 mg to about 250 mg, about 60 mg to about 250 mg, about 70 mg to about 250 mg, about 80 mg to about 250 mg, about 90 mg to about 250 mg, about 100 mg to about 250 mg, about 110 mg to about 250 mg, about 120 mg to about 250 mg, about 130 mg to about 250 mg, about 140 mg to about 250 mg, about 150 mg to about 250 mg, about 160 mg to about 250 mg, about 170 mg to about 250 mg, about 180 mg to about 250 mg, about 190 mg to about 250 mg, about 200 mg to about 250 mg, about 210 mg to about 250 mg, about 220 mg to about 250 mg, about 230 mg to about 250 mg, about 240 mg to about 250 mg; about 250 mg to about 500 mg, about 260 mg to about 500 mg, about 270 mg to about 500 mg, about 280 mg to about 500 mg, about 290 mg to about 500 mg, about 300 mg to about 500 mg, about 310 mg to about 500 mg, about 320 mg to about 500 mg, about 330 mg to about 500 mg, about 340 mg to about 500 mg, about 350 mg to about 500 mg, about 360 mg to about 500 mg, about 370 mg to about 500 mg, about 380 mg to about 500 mg, about 390 mg to about 500 mg, about 400 mg to about 500 mg, about 410 mg to about 500 mg, about 420 mg to about 500 mg, about 430 mg to about 500 mg, about 440 mg to about 500 mg, about 450 mg to about 500 mg, about 460 mg to about 500 mg, about 470 mg to about 500 mg, about 480 mg to about 500 mg, or about 490 mg to about 500 mg.

In one embodiment described herein, the abuse deterrent oral composition described herein may comprise an active pharmaceutical ingredient load (e.g., drug load) of about 1% to about 90%, including each integer within the specified range. In one embodiment, the drug load can comprise about 1%, about 2%, about 2.5%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or even higher. In one aspect, the drug load is about 20%. In one aspect, the drug load is about 25%. In one aspect, the drug load is about 30%. In one aspect, the drug load is about 35%. In one aspect, the drug load is about 40%. In one aspect, the drug load is about 50%. In one aspect, the drug load is about 60%. In one aspect, the drug load is about 28%. In one aspect, the drug load is about 32%. In one aspect, the drug load is about 44%. In one embodiment, the drug load is about 48%.

In one embodiment, the active pharmaceutical ingredient is tapentadol, or a salt, ether, ester, variant, or derivative thereof. In one embodiment, the active pharmaceutical ingredient is tapentadol hydrochloride (tapentadol.HCl). See Prescribing Information for Nucynta® 09/2013 and Nucynta® ER 04/2014 (Jansen Pharmaceuticals Inc.; available at: www.nucynta.com), which are incorporated by reference herein for such teachings.

In one aspect, the dose of tapentadol is 20 mg. In another aspect, the dose of tapentadol is 25 mg. In another aspect, the dose of tapentadol is 50 mg. In another aspect, the dose of tapentadol is 75 mg. In another aspect, the dose of tapentadol is 100 mg. In another aspect, the dose of tapentadol is 150 mg. In another aspect, the dose of tapentadol is 200 mg. In another aspect, the dose of tapentadol is 250 mg. In another aspect, the dose of tapentadol is 300 mg. In another aspect, the dose of tapentadol is 350 mg. In another aspect, the dose of tapentadol is 400 mg. In another aspect, the dose of tapentadol is 450 mg. In another aspect, the dose of tapentadol is 500 mg.

In another embodiment, the total dosage of tapentadol administered in a 24-hour period is about 20 mg to about 600 mg per 24-hour period. In one aspect, the total dosage of tapentadol administered in a 24-hour period is about 50 mg to about 250 mg per 24-hour period. The dosage can contain a total amount of tapentadol effective for treatment, amelioration, prophylaxis, or reducing the onset of or symptoms of pain.

In one embodiment, the recommended dosage is based upon the condition of the subject in need thereof. The subject can comprise a human or mammal in need thereof. In one aspect, the need is defined as a painful condition or perception of pain. In one embodiment, the perception of pain is described as a numerical scale. In one aspect, this numerical scale indicates 0 for no pain, 1-3 suggestive of mild pain; annoying or nagging pain that does not affect the activities of daily life, 4-6 for moderate pain that interferes significantly with the activities of daily life, and 7-10 for severe pain that is disabling for which the activities of daily life are not possible. Another aspect described herein comprises orally administering a maximal dosage of about 50 mg to about 100 mg of tapentadol every 24 hours for humans or mammals with a pain of 1-3. Another aspect described herein comprises orally administering a maximal dosage of about 100 mg to about 400 mg of tapentadol every 24 hours for humans or mammals with a pain of 4-6. Another aspect described herein comprises orally administering a maximal dosage of 400 mg to about 600 mg of tapentadol every 24 hours for humans or mammals with a pain of 7-10. In one aspect, the level of pain is assessed by observing the human or mammal.

Another aspect described herein comprises orally administering an additional dosage of about 50 mg to about 100 mg of tapentadol after 1 hour from the administration of a first dose if pain of any type is not ameliorated in the human or mammal in need thereof. Another aspect described herein comprises orally administering additional dosages of about 50 mg to about 100 mg of tapentadol every 4 to 6 hours if pain of any type is not ameliorated in the human or mammal in need thereof.

Another aspect described herein comprises orally administering a delayed release dosage of about 50 mg of an active pharmaceutical ingredient every 12 hours for a human or mammal with a pain of 1-3. Another aspect described herein comprises orally administering a delayed release dosage of about 150 mg of tapentadol every 12 hours for a human or mammal with a pain of 4-6. Another aspect described herein comprises orally administering a delayed release dosage of about 250 mg of tapentadol every 12 hours for a human or mammal with a pain of 7-10. Another aspect described herein comprises increasing the delayed release dosage of tapentadol by 50 mg increments every 24 hours to a maximal daily dosage of 600 mg if pain of any type is not ameliorated in the human or mammal in need thereof. Another aspect described herein comprises decreasing the dosage of tapentadol as needed every 24 hours if pain of any type has decreased or has been ameliorated in the human or mammal in need thereof.

Additional pain that the abuse deterrent pharmaceutical composition described herein may be useful for the treatment of pain stemming from including, but not limited to, chronic arthritis, osteoarthritis, rheumatoid arthritis, acute tendonitis, bursitis, headaches, migraines, chronic neuropathies, shingles, premenstrual symptoms, sports injuries, malignancy, radiculopathy, sciatica/sciatic pain, sarcoidosis, necrobiosis, lipoidica, or granuloma annulare.

Another embodiment described herein is an abuse deterrent pharmaceutical composition as described herein for administration to a subject having pain, comprising a therapeutically effective amount of one or more active pharmaceutical ingredients, wherein the subject achieves a reduction of pain relative to baseline without substantially experiencing one or more side effects including, but not limited to, headache, vertigo, somnolence, nausea, constipation, vomiting, xerostomia, fatigue, pruritus, eructation, heartburn, abdominal discomfort, or loss of appetite.

Another embodiment described herein is an abuse deterrent pharmaceutical composition as described herein for administration to a subject having pain, comprising a therapeutically effective amount of one or more active pharmaceutical ingredients exhibiting an in vitro dissolution rate at pH 2.4 comprising about 20% to about 80% dissolution after about 60 minutes to about 720 minutes including each integer within the specified ranges of dissolution and time. In another aspect, the in vitro dissolution rate at pH 2.4 is about 50% after about 280 minutes to about 720 minutes, including each integer with in the specified time range. In one aspect, the in vitro dissolution rate at pH 2.4 about 50% after about 60 min, about 50% after about 70 min, about 50% after about 80 min, about 50% after about 90 min, about 50% after about 120 min, about 50% after about 150 min, about 50% after about 180 min, about 50% after about 210 min, about 50% after about 240 min, about 50% after about 300 min, is about 50% after about 330 min, about 50% after about 360 min, is about 50% after about 390 min, about 50% after about 420 min, about 50% after about 480 min, about 50% after about 540 min, about 50% after about 600 min, about 50% after about 660 min, about 50% after about 720 min, about 50% after about 780 min, about 50% after about 840 min, about 50% after about 900 min, about 50% after about 960 min, or about 50% after 1080 min.

In another embodiment, the abuse deterrent pharmaceutical composition as described herein has an in vitro dissolution rate at pH 2.4 of about 50% after about 1 hour, about 50% after about 2 hours, about 50% after about 3 hours, about 50% after about 4 hours, about 50% after about 5 hours, about 50% after about 6 hours, about 50% after about 7 hours, about 50% after about 8 hours, about 50% after about 9 hours, about 50% after about 10 hours, about 50% after about 11 hours, about 50% after about 12 hours, about 50% after about 13 hours, about 50% after about 14 hours, about 50% after about 15 hours, about 50% after about 16 hours, about 50% after about 17 hours, or about 50% after about 18 hours.

In another embodiment, the abuse deterrent pharmaceutical composition as described herein has an in vitro dissolution rate at pH 2.4 of about 50% after about 240 to about 480 minutes. In another aspect, the in vitro dissolution rate at pH 2.4 is about 50% after about 300 to about 480 minutes. In another aspect, the in vitro dissolution rate at pH 2.4 is about 50% after about 320 to about 420 minutes. In another aspect, the in vitro dissolution rate at pH 2.4 is about 50% after about 300 to about 400 minutes. In another aspect, the in vitro dissolution rate at pH 2.4 is about 50% after about 320 minutes. In another aspect, the in vitro dissolution rate at pH 2.4 is about 50% after about 340 minutes. In another aspect, the in vitro dissolution rate at pH 2.4 is about 50% after about 360 minutes. In another aspect, the in vitro dissolution rate at pH 2.4 is about 50% after about 380 minutes. In another aspect, the in vitro dissolution rate at pH 2.4 is about 50% after about 400 minutes. In another aspect, the in vitro dissolution rate at pH 2.4 is about 50% after about 420 minutes. In another aspect, the in vitro dissolution rate at pH 2.4 is about 50% after about 440 minutes. In another aspect, the in vitro dissolution rate at pH 2.4 is about 50% after about 480 minutes. In another aspect, the in vitro dissolution rate at pH 2.4 is about 50% after about 500 minutes.

Another embodiment described herein is an abuse deterrent pharmaceutical composition as described herein comprising a therapeutically effective amount of one or more active pharmaceutical ingredients for administration to a subject having pain, exhibiting an vitro dissolution rate at pH 2.4, of about 50% after about 240 to about 480 minutes.

Another embodiment described herein is an abuse deterrent pharmaceutical composition as described herein comprising a therapeutically effective amount of one or more active pharmaceutical ingredients for administration to a subject having pain, exhibiting an in vitro dissolution rate at pH 2.4, as described herein in any one of Drawings 4-9.

Another embodiment described herein is a method for orally administering a dosage form of an abuse deterrent pharmaceutical composition comprising an active pharmaceutical ingredient described herein for the treatment, amelioration, prophylaxis, or reducing the onset of or symptoms of pain.

Another embodiment described herein is a method for treating, retarding the progression of, delaying the onset of, prophylaxis of, amelioration of, or reducing the symptoms of pain, comprising administering to a subject in need thereof an oral pharmaceutical composition as described herein comprising a therapeutically effective amount of one or more active pharmaceutical ingredients for administration to a subject having pain, wherein the pharmaceutical composition exhibits about a 50% in vitro dissolution rate at pH 2.4, comprising about 40% to about 60% dissolution after about 240 minutes to about 480 minutes.

Another embodiment described herein is a method for treating, retarding the progression of, delaying the onset of, prophylaxis of, amelioration of, or reducing the symptoms of pain, comprising administering to a subject in need thereof an oral pharmaceutical composition as described herein comprising a therapeutically effective amount of one or more active pharmaceutical ingredients for administration to a subject having pain, exhibiting an in vitro dissolution rate at pH 2.4, as described herein in any one of Drawings 4-9.

Another embodiment described herein is a method for treating, retarding the progression of, prophylaxis of, delaying the onset of, ameliorating, or reducing the symptoms of pain comprising the administration of a therapeutically effective amount of one or more abuse deterrent pharmaceutical compositions described herein to a subject with pain, wherein the administration is sufficient to achieve a reduction pain relative to baseline in the subject without substantially inducing one or more side effects including, but not limited to, headache, vertigo, somnolence, nausea, constipation, vomiting, xerostomia, fatigue, pruritus, eructation, heartburn, abdominal discomfort, or loss of appetite.

In another embodiment, the abuse deterrent pharmaceutical composition described herein is contained and dispensed from a tamper evident packaging. The term "tamper evident" or "tamper resistant" refers to a packaging of any kind that readily displays or allows for an individual to observe any physical interference or manipulation of said packaging. The tamper evident packaging provides reasonable evidence to consumers that tampering has occurred. The tamper evident packaging additionally contains appropriate labelling statements describing the features and evidences of the tamper evident packaging. In one aspect, the tamper evident packaging comprises: bottles, film wrappers, blister or strip packs, bubble packs, heat shrink bands or wrappers, foil, paper, or plastic pouches, container mouth inner seals, tape seals, breakable caps, sealed metal tubes or plastic heat-sealed tubes, sealed cartons, aerosol containers, cans including metal and composite materials, or any combination thereof. The packaging may also contain appropriate instructions for prescribing, instructions for use, warnings, or other appropriate information.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of the specified embodiments. All of the various embodiments, aspects, and options disclosed herein can be combined in all variations. The scope of the compositions, formulations, methods, and processes described herein include all actual or potential combinations of embodiments, aspects, options, examples, and preferences herein described. All patents and publications cited herein are incorporated by reference herein for the specific teachings thereof.

EXAMPLES

Example 1

Abuse deterrent matrices as described herein were prepared using the composition shown in Table 6. The composition was prepared according to the method of Example 3 and encapsulated in a soft capsule shell.

TABLE 6

Exemplary Abuse Deterrent Controlled Release Matrix Composition

| Ingredient | Percentage (%) |
| --- | --- |
| Olive Oil | 38.3 |
| Gelucire ® 43/01 | 11.3 |
| Pluronic ® F127 | 6.5 |
| Kollidon ® 90 F | 4.7 |

TABLE 6-continued

Exemplary Abuse Deterrent Controlled Release Matrix Composition

| Ingredient | Percentage (%) |
| --- | --- |
| Carbopol ® 971 A | 3.1 |
| Meglumine | 2.4 |
| EUDRAGIT ® EPO | 4.61 |
| Tapentadol HCl | 29.2 |
| TOTAL | 100 |

Example 2

Further abuse deterrent matrices as described herein were prepared using the compositions shown in Table 7 and Table 8. The compositions were prepared and encapsulated in a soft capsule shell.

TABLE 7

Exemplary Abuse Deterrent Controlled Release Matrix Composition

| Ingredients | Mass (g) | Percentage (%) |
| --- | --- | --- |
| Soybean Oil | 32.0 | 46.82 |
| Aerosil ® | 0.9 | 1.32 |
| Gelucire ® 43/01 | 2.0 | 2.93 |
| Bee's wax | 2.0 | 2.93 |
| HPMC 4M | 4.0 | 5.85 |
| Kollidon ® 90 F | 4.5 | 6.58 |
| Carbopol ® 971 A | 1.25 | 1.83 |
| EUDRAGIT ® EPO | 3.5 | 5.12 |
| Tapentadol HCl | 18.2 | 26.63 |
| TOTAL | 68.35 | 100.00 |

TABLE 8

Exemplary Abuse Deterrent Controlled Release Matrix Composition

| Ingredients | Mass (g) | Percentage (%) |
| --- | --- | --- |
| Soybean Oil | 50.53 | 50.53 |
| Aerosil ® | 0.89 | 0.89 |
| Gelucire ® 43/01 | 2.04 | 2.04 |
| Bee's wax | 1.77 | 1.77 |
| HPMC 4M | 6.45 | 6.45 |
| PEO (N10; 100,000) | 9.68 | 9.68 |
| Carbopol ® 971 A | 0.89 | 0.89 |
| EUDRAGIT ® EPO | 2.94 | 2.94 |
| Tapentadol HCl | 24.87 | 24.87 |
| TOTAL | 100 | 100.00 |

Example 3

An exemplary abuse deterrent controlled release matrix composition as described herein comprises a liquid lipophilic vehicle, a semisolid lipophilic vehicle, a non-ionic surfactant, a hygroscopic polymer, one or more pH buffering agents, one or more hydrophilic polymers, and an active pharmaceutical ingredient. The abuse deterrent matrices described herein comprise one or more semi-solid lipophilic vehicles, one or more hygroscopic polymers, one or more hydrophilic polymers, a suspension agent, and an active pharmaceutical ingredient. The process for preparing an abuse deterrent controlled release matrix includes preparing a composition of one or more lipid or lipophilic vehicles, one or more hygroscopic polymers, one or more hydrophilic polymers, optionally one or more non-ionic surfactant, optionally one or more pH buffering agent(s), optionally one or more suspension agents, and one or more active pharmaceutical ingredient by heating said mixture from between 45° C. and 80° C. with stirring or agitation in a suitable vessel. The process further comprises decreasing the matrix mixture temperature to between about 25° C. and about 45° C. followed by a homogenization step, wherein the matrix is homogenized to be substantially flowable. Prior to encapsulation in a soft gel capsule described herein, the matrix is deaerated at a temperature of about 25° C. to about 45° C.

The process for manufacturing a soft capsule comprising the pharmaceutical composition as described herein includes preparing a gel mass for a soft capsule; casting the gel mass into films or ribbons using heat-controlled drums or surfaces; and manufacturing a soft capsule comprising a matrix fill using rotary die technology. During this process, the abuse deterrent controlled release matrix is injected in to the lumen as the soft capsule is formed by rotary die encapsulation. The soft capsule can be a typical soft capsule ("softgel") or an enteric soft capsule.

Example 4

The abuse deterrent controlled release matrix composition shown in Table 6, generated by the methods described herein and encapsulated in a soft gel capsule as described herein, was tested on its resistance to physical tampering and its stability in various conditions.

The abuse deterrent controlled release oral composition described herein, was further tested for its resistance to physical tampering by chewing/crushing, grating, grinding, and cutting. For chewing/crushing studies, the abuse deterrent oral composition described herein was placed in a mortar and was crushed by using a pestle under ambient conditions. Physical observations after crushing were used to make conclusions about the chewability and physical strength of the composition. For grating studies, the abuse deterrent controlled release oral composition described herein was hand-grated across a common cheese grater under ambient conditions. For grinding studies, the abuse deterrent oral composition described herein was placed in a coffee grinder under ambient conditions and ground. For cutting studies, the abuse deterrent controlled release oral composition described herein was cut with a knife or a lab cutter. These experiments were fully carried out as described under ambient conditions (25° C.), heated conditions, wherein the abuse deterrent oral composition described herein was heated for two hours (40° C.), and refrigerated conditions, wherein the abuse deterrent controlled release oral composition described herein was frozen for two hours (0° C.). As shown in FIGS. 1-3, the abuse deterrent oral composition described herein, was resistant to being dispersed, dissolved, or extracted in the studies utilizing the methods described above.

The abuse deterrent controlled release oral composition described herein was subjected to a series of stability experiments. In these experiments, the abuse deterrent controlled release oral composition described herein was cut in half with a razor blade. The first experiment was a non-enzymatic dissolution study, wherein the abuse deterrent controlled release oral composition described herein was suspended in 900 mL of simulated intestinal fluid (SIF) at a temperature of 37° C. The percentage of tapentadol released from the matrix was assessed at 9 time points over a time period of 800 minutes as shown in FIG. 4.

Figure 5:
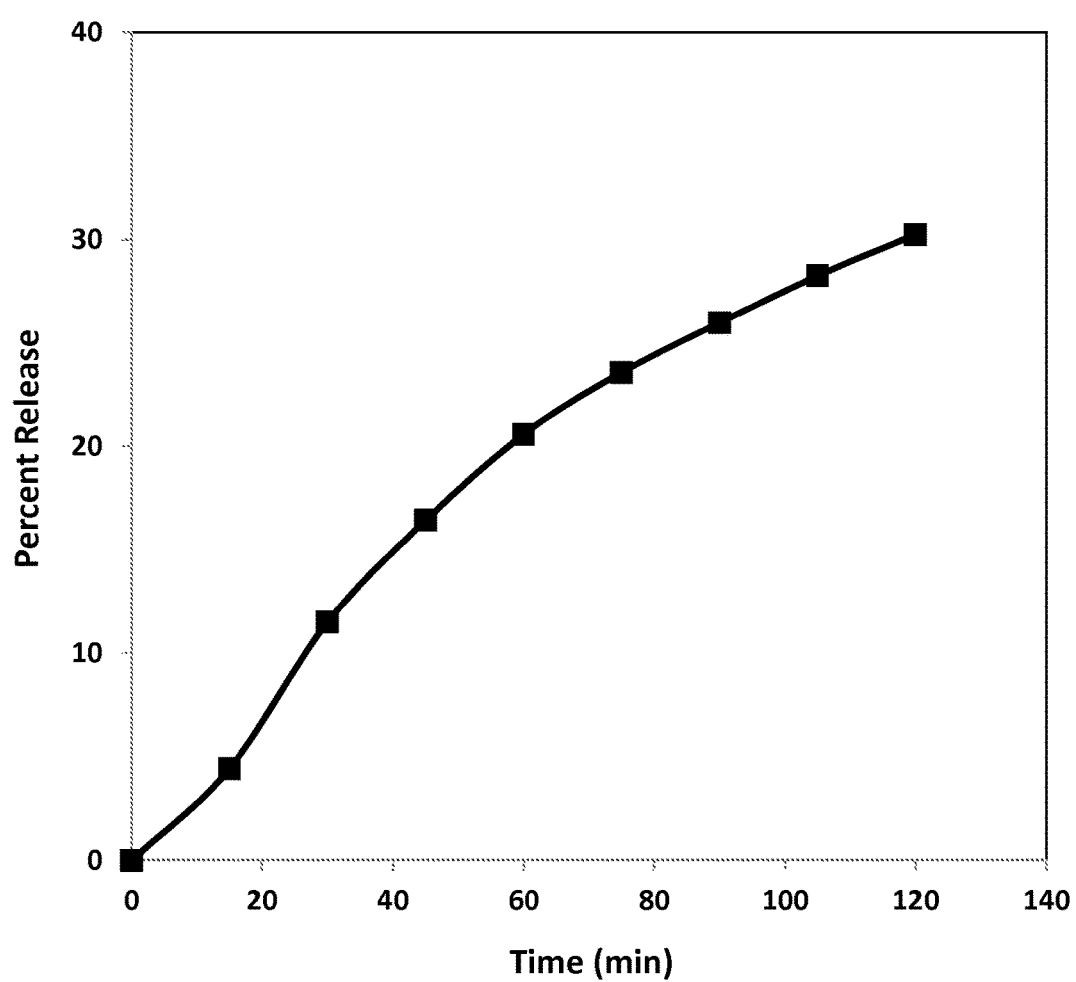
FIG. 5. Release profile of a soft capsule comprising the composition of Table 6 in 900 mL of 40% ethanol, 60% 0.1N HCl (pH 2.4) at 100 rpm and 37° C.

Next, the abuse deterrent controlled release oral composition described herein was shown to not immediately release tapentadol when placed in alcohol as shown in FIG. 5. These studies were performed by suspending the abuse deterrent oral composition described herein was suspended in a 900 mL solution of 40% ethanol and 60% 0.1N HCl and agitated with paddles at 100 RPM at 37° C. for 120 minutes. The percentage of tapentadol released from the matrix was assessed at 9-time points over a time period of 120 minutes.

Figure 6:
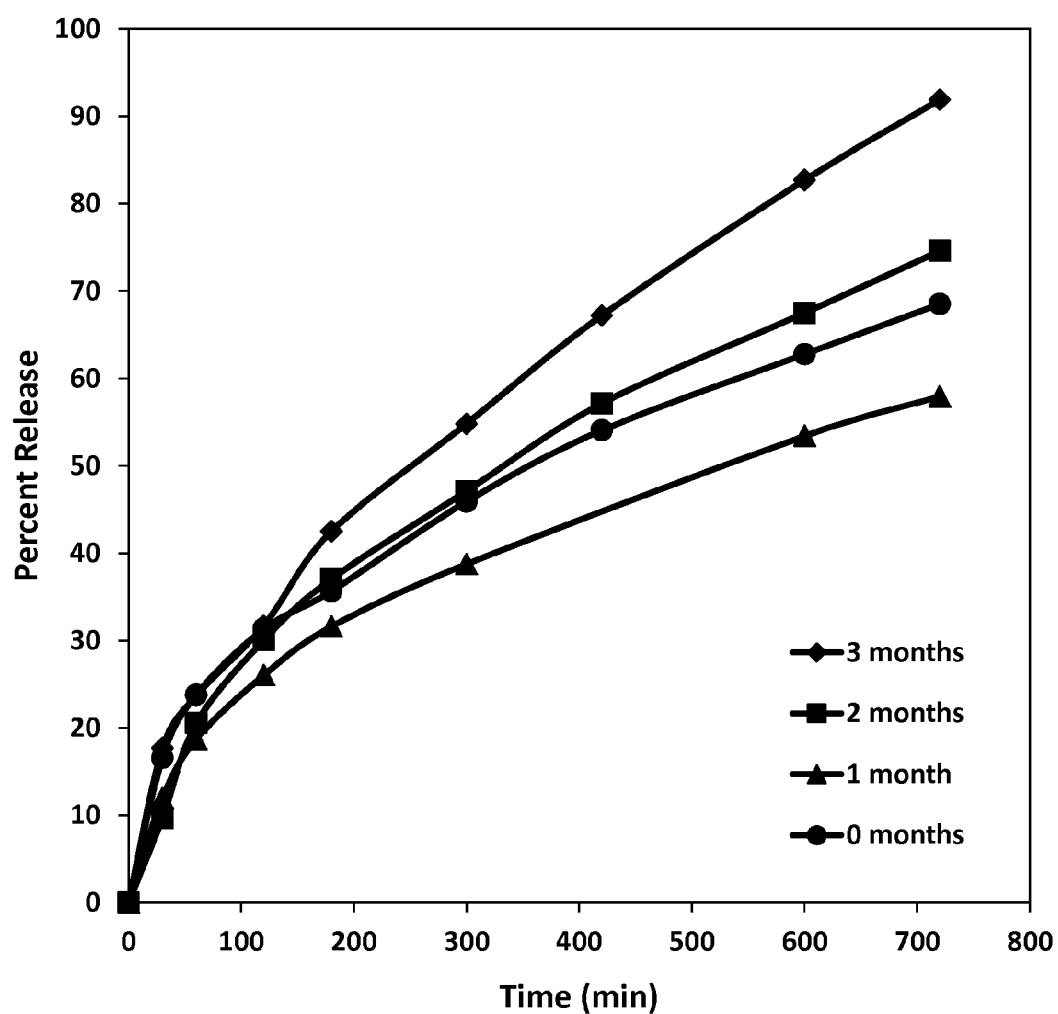
FIG. 6. Release profile of a soft capsule comprising the composition of Table 6 in phosphate buffer (pH 6.8) after storage at 40° C., 75% relative humidity.

Further testing showed that the abuse deterrent oral composition described herein retained its controlled release properties after being stored at 40° C. at a relative humidity (RH) for up to three months as shown in FIG. 6. Samples were taken after 1 month, 2 months, and 3 months of time and the percentage of tapentadol released from the matrix was assessed at 9-time points over a time period of 800 minutes.

Figure 7:
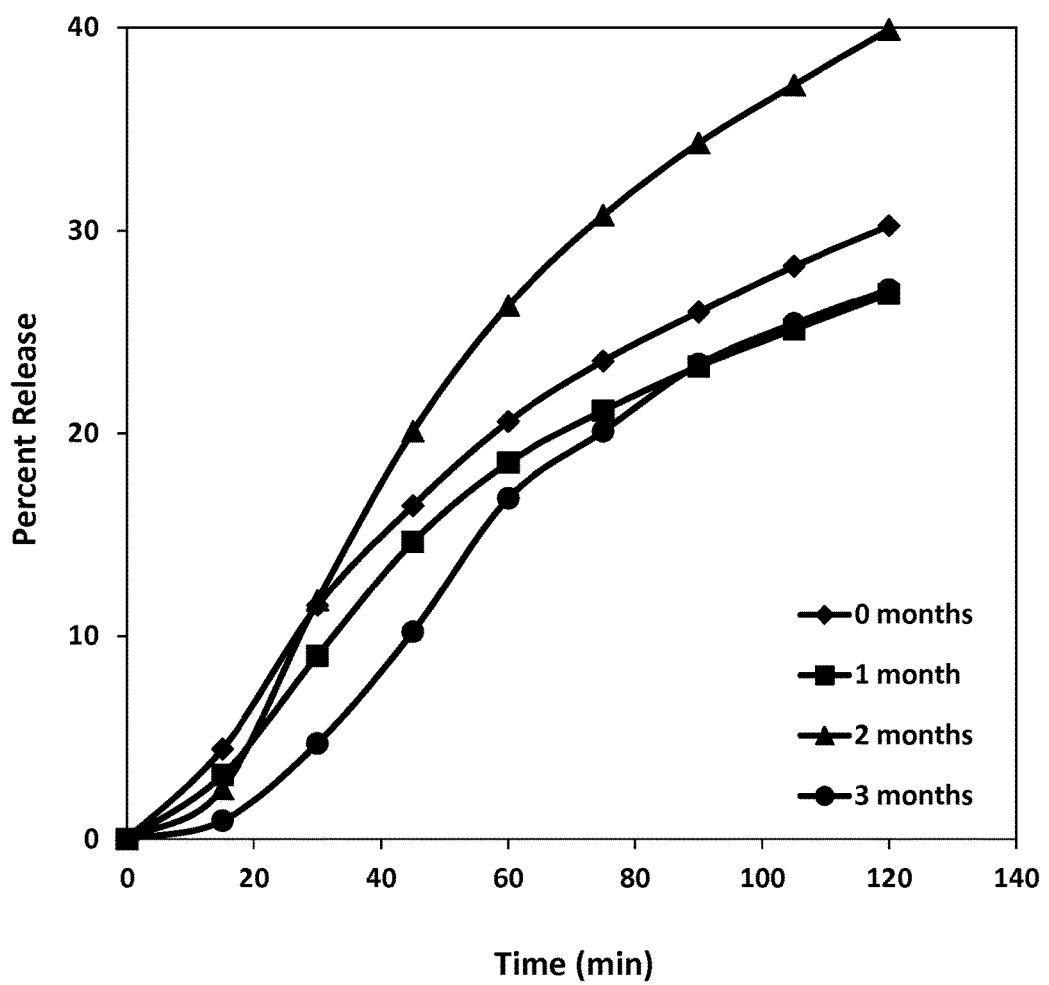
FIG. 7. Release profile of a soft capsule comprising the composition of Table 6 in 40% ethanol, 60% 0.1N HCl (pH 2.4) after storage at 40° C., 75% relative humidity.

As shown in FIG. 7, the abuse deterrent oral composition described herein, did not release tapentadol immediately in ethanol after prolonged storage for up to 3 months at 40° C. at a RH of 75%. The effects of long term storage of the abuse deterrent oral composition described herein on its susceptibility to ethanol extraction was assessed by suspending the abuse deterrent oral composition described herein, in a 900 mL solution of 40% ethanol and 60% 0.1N HCl followed by agitation with paddles at 100 RPM at 37° C. for 120 minutes. The percentage of tapentadol released from the abuse deterrent controlled release matrix described herein was assessed at 9-time points over a time period of 120 minutes.

Example 5

The abuse deterrent controlled release matrix compositions shown in Table 7, generated by the methods described herein and encapsulated in a soft gel capsule as described herein, were tested on their respective stability and dissolution kinetics.

Figure 8:
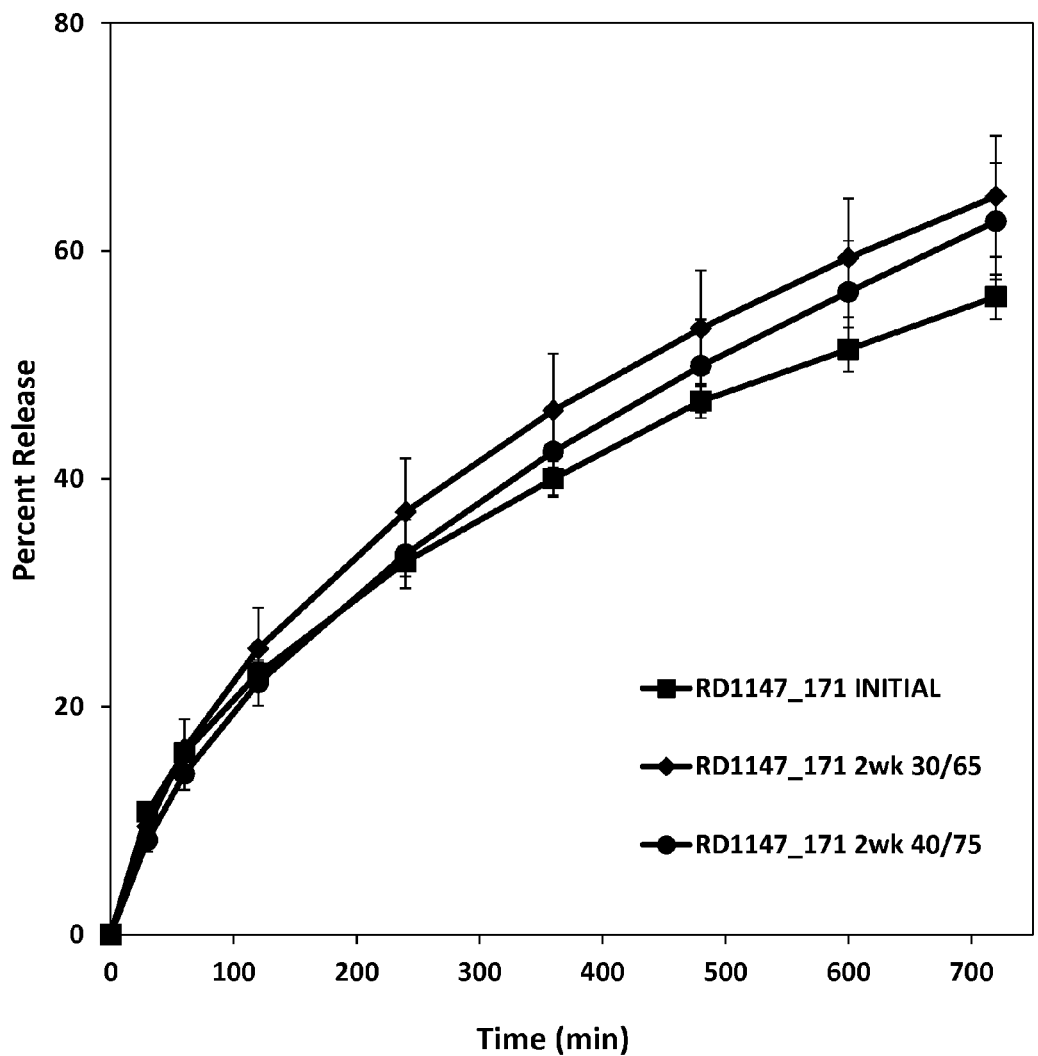
FIG. 8. Release profile of a soft capsule comprising the composition of Table 7 in phosphate buffer (pH 6.8) initially, after storage for 2 weeks at 30° C., 65% relative humidity, and after storage for 2 weeks at 40° C., 75% relative humidity.

As shown in FIG. 8, the abuse deterrent oral composition of Table 7 retained its controlled release properties after being stored at 30° C. at a relative humidity (RH) of 65% or at 40° C. at a relative humidity (RH) of 75% for up to two weeks. Samples were taken at 0 weeks or at two weeks for the above noted conditions and the percentage of tapentadol released from the matrix was assessed at 9-time points over a time period of 12 hours (720 min) during agitation in phosphate buffer, pH 6.8, at 37° C. with paddles at 100 RPM.

Example 6

The abuse deterrent controlled release matrix compositions shown in Table 8 generated by the methods described herein and encapsulated in a soft gel capsule as described herein, were tested on their respective dissolution kinetics and abuse deterrence in ethanol.

Figure 9:
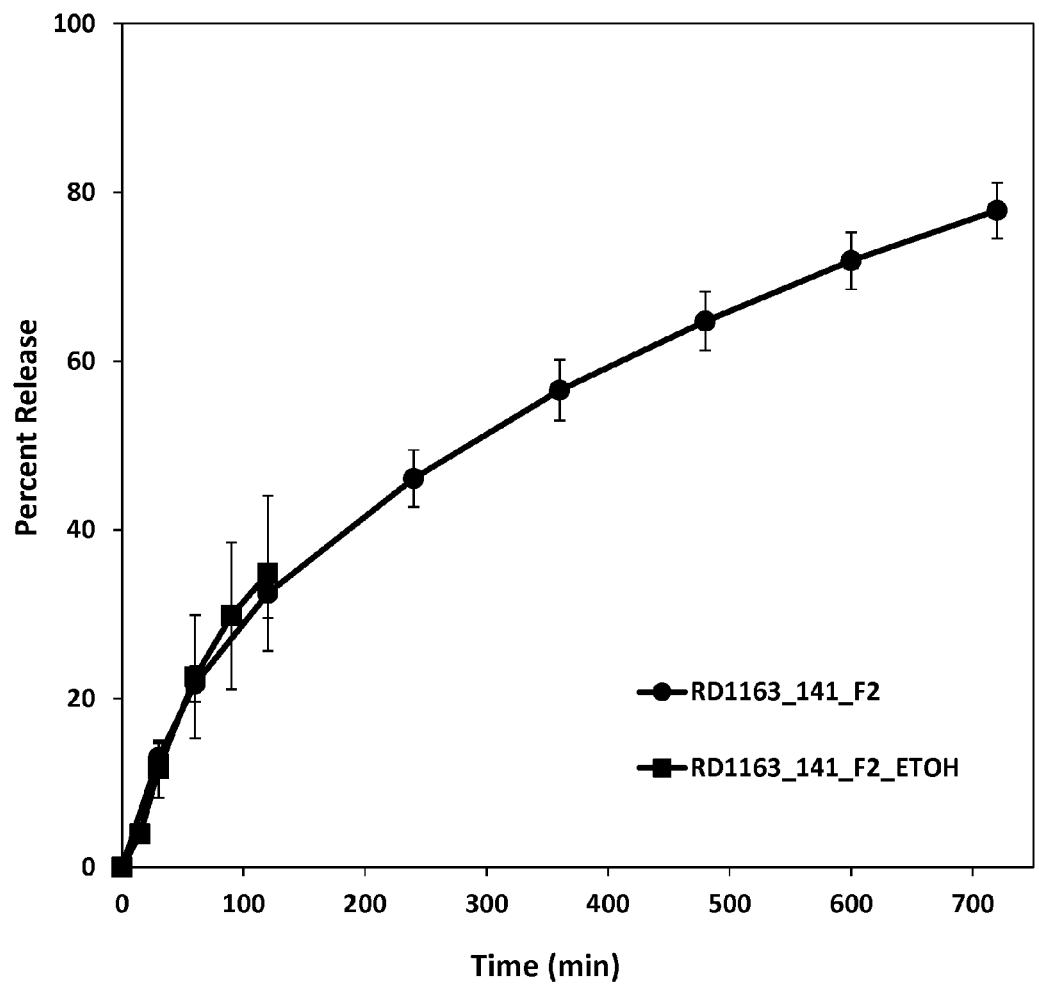
FIG. 9. Release profile of a soft capsule comprising the composition of Table 8 in 40% ethanol, 60% 0.1N HCl (pH 2.4).

As shown in FIG. 9, the abuse deterrent oral composition of Table 8 retained its controlled release properties in a dissolution buffer or an ethanol buffer. Samples were taken and the percentage of tapentadol released from the matrix was assessed over a time period of 12 hours (720 min) in a solution of 40% ethanol and 60% 0.1N HCl, pH 2.4, during agitation with paddles at 100 RPM at 37° C.

Example 7

Examples of abuse deterrent controlled release properties of the abuse deterrent controlled release matrix described herein to prevent tapentadol release in different solvents, including water, coffee, vinegar, cola, milk, and isopropanol are shown in Table 9. These tests were conducted by placing the soft gel capsule containing the abuse deterrent controlled release matrix in a transparent beaker with 100 mL of the indicated solvent and shaking the beaker at 75 RPM and 37° C. for 2 hours. The percentage of tapentadol released was assessed after 5, 20, 60, and 120-minute time points. HPLC was used to detect the released tapentadol.

TABLE 9

Tapentadol•HCl Release in Solvents at 37° C. 75 rpm (n = 3)

| Solvent | Percent Released (%) 250 mg soft gel capsule | | | |
|---|---|---|---|---|
| | 5 min | 20 min | 60 min | 120 min |
| Water | 2% | 1% | 9% | 9% |
| Coffee | 0% | 0% | 16% | 21% |
| Vinegar | 0% | 0% | 0% | 10% |
| Cola | 0% | 0% | 0% | 21% |
| Milk of Magnesia | 0% | 0% | 6% | 21% |
| Milk | 0% | 1% | 3% | 9% |
| Isopropanol (97.7%) | 0% | 0% | 0% | 0% |

Example 8

Examples of abuse deterrent controlled release properties of the abuse deterrent controlled release matrix described herein to prevent tapentadol release in buffers of different pH values are shown in Table 10. These tests were conducted by placing the soft gel capsule containing the abuse deterrent controlled release matrix in a transparent beaker with 100 mL of the indicated pH solvent and shaking the beaker at 75 RPM and 37° C. for 2 hours. The percentage of tapentadol released was assessed after 5, 20, 60, and 120-minute time points.

TABLE 10

Tapentadol•HCl release in Different pH Values at 37° C., 100 rpm (n = 3)

| pH | Percent Released (%) 250 mg soft gel capsule | | | |
|---|---|---|---|---|
| | 5 min | 20 min | 60 min | 120 min |
| pH 1 | 0% | 0% | 3% | 6% |
| pH 4 | 0% | 0% | 2% | 6% |
| pH 6 | 0% | 0% | 2% | 6% |
| pH 8 | 0% | 0% | 2% | 5% |
| pH 12 | 0% | 0% | 1% | 4% |

Example 9

Examples of abuse deterrent controlled release properties of the abuse deterrent controlled release matrix described herein to prevent tapentadol release indifferent concentrations of ethanol are shown in Table 11. These tests were conducted by placing the soft gel capsule containing the abuse deterrent controlled release matrix in a transparent beaker with 100 mL of the indicated ethanol solution and shaking the beaker at 75 RPM and 37° C. for 2 hours. The percentage of tapentadol released was assessed after 5, 20, 60, and 120-minute time points.

TABLE 11

Tapentadol•HCl Release in Ethanol Solutions at 37° C., rpm (n = 3)

| Ethanol (%) v/v | Percent Released (%) 250 mg soft gel capsule | | | |
|---|---|---|---|---|
| | 5 min | 20 min | 60 min | 120 min |
| 0% Ethanol | 2% | 1% | 9% | 9% |
| 5% Ethanol | 0% | 0% | 2% | 6% |
| 20% Ethanol | 0% | 0% | 1% | 3% |
| 40% Ethanol | 0% | 0% | 1% | 4% |

Example 10

Examples of abuse deterrent controlled release properties of the abuse deterrent controlled release matrix described herein to prevent tapentadol release in different concentrations of different solvents, including 95% ethanol, methanol, acetone, ethyl acetate, paint thinner, mineral spirits, bleach, 0.1N HCl, 0.1N acetic acid, 0.1N NaOH, and 0.1N NaHCO$_3$ are shown in Table 12. These tests are conducted after cutting the soft gel capsule and placing it in a transparent beaker with 100 mL of the indicated ethanol solution and shaking the beaker at 75 RPM and 37° C. for 2 hours. The percentage of tapentadol released is assessed after 5, 20, 60, and 120-minute time points.

TABLE 12

Tapentadol•HCl Release in Solvents at 37° C.

| Solvent | Amount Released from 250 mg soft gel capsule | | | |
|---|---|---|---|---|
| | 5 min | 20 min | 60 min | 120 min |
| Ethanol, 95% | pass | pass | pass | pass |
| Methanol | pass | pass | pass | pass |
| Isopropanol | pass | pass | pass | pass |
| Acetone | pass | pass | pass | pass |
| Ethyl acetate | pass | pass | pass | pass |
| Paint Thinner | pass | pass | pass | pass |
| Mineral Spirits | pass | pass | pass | pass |
| Bleach (NaClO) | pass | pass | pass | pass |
| 0.1N HCl | pass | pass | pass | pass |
| 0.1N acetic acid | pass | pass | pass | pass |
| 0.1N NaOH | pass | pass | pass | pass |
| 0.1N NaHCO$_3$ | pass | pass | pass | pass |

"pass" indicates an insignificant amount is released.

Example 11

Additional exemplary gel mass compositions useful for producing abuse deterrent controlled release soft gel capsules as described herein are shown in Tables 13-16. Composition components are set forth by weight percentage of the total weight of the gel mass composition. Such compositions may be encapsulated in soft capsules or enteric soft capsules.

TABLE 13

Exemplary Abuse Deterrent Controlled Release Matrix Compositions

| Ingredient | Weight Percentage (%) | | | | | |
|---|---|---|---|---|---|---|
| | EX 1 | EX 2 | EX 3 | EX 4 | EX 5 | EX 6 |
| Total Lipophilic Vehicle (TLV) | 58.0 | 92.0 | 38.0 | 50.0 | 31.0 | 47.0 |

TABLE 13-continued

Exemplary Abuse Deterrent Controlled Release Matrix Compositions

|  | | | | | | |
|---|---|---|---|---|---|---|
| Non-ionic Surfactant (NIS) | 15.0 | 3.5 | 7.0 | 6.0 | 1.0 | 11.0 |
| Hygroscopic Polymer (HP) | 1.0 | 1.0 | 10.0 | 4.7 | 5.0 | 9.0 |
| Total Hydrophilic Polymer (THP) | 12.0 | 2.0 | 7.3 | 7.7 | 10.0 | 20.0 |
| pH Buffering Agent (BA) | 4.0 | 0.5 | 2.8 | 2.4 | 3.0 | 8.0 |
| Active Pharmaceut. Ingredient (API) | 10.0 | 1.0 | 35.0 | 29.2 | 50.0 | 5.0 |
| TOTAL | 100 | 100 | 100 | 100 | 100 | 100 |

Components and Relational Ratios

| | EX 1 | EX 2 | EX 3 | EX 4 | EX 5 | EX 6 |
|---|---|---|---|---|---|---|
| Hydrophilic Matrix Comp. (HMC) | 32.0 | 7.0 | 27.0 | 20.8 | 19.0 | 48.0 |
| Total Matrix Mass | 90.0 | 99.0 | 65.0 | 70.8 | 50.0 | 95.0 |
| Ratio Liquid to Semisolid Lipid | 2.6 | 1.9 | 4.4 | 2.6 | 4.2 | 2.9 |
| Ratio NIS to HP | 15.0 | 3.5 | 0.7 | 1.3 | 0.2 | 1.2 |
| Ratio of Anionic Pol.:Cationic Pol. | 0.7 | 1.0 | 0.7 | 0.7 | 0.7 | 0.7 |
| Ratio of TLV to HP + NIS | 3.6 | 20.4 | 2.2 | 4.7 | 5.2 | 2.4 |
| Ratio of BA to THP | 0.3 | 0.3 | 0.4 | 0.3 | 0.3 | 0.4 |
| Ratio of TLV to HMC | 1.8 | 13.1 | 1.4 | 2.4 | 1.6 | 1.0 |
| Ratio of API to HMC | 0.3 | 0.1 | 1.3 | 1.4 | 2.6 | 0.1 |
| Ratio of API to TLV | 0.2 | 0.01 | 0.9 | 0.6 | 1.6 | 0.1 |
| Ratio API to Total Matrix | 0.1 | 0.01 | 0.5 | 0.4 | 1.0 | 0.1 |

TABLE 14

Exemplary Abuse Deterrent Controlled Release Matrix Compositions

Weight Percentage (%)

| Ingredient | EX 1 | EX 2 | EX 3 | EX 4 | EX 5 | EX 6 |
|---|---|---|---|---|---|---|
| Total Lipophilic Vehicle (TLV) | 67.5 | 65.0 | 44.0 | 50.0 | 29.0 | 32.0 |
| Hygroscopic Polymer (HP) | 10.0 | 23.0 | 13.0 | 13.0 | 11.5 | 18.0 |
| Total Hydrophilic Polymer (THP) | 10.5 | 6.0 | 7.0 | 5.6 | 9.0 | 4.4 |
| Stabilizing agent (SA) | 2.0 | 5.0 | 1.0 | 2.2 | 0.5 | 0.6 |
| Active Pharmaceut. Ingredient (API) | 10.0 | 1.0 | 35.0 | 29.2 | 50.0 | 45.0 |
| TOTAL | 100 | 100 | 100 | 100 | 100 | 100 |

Components and Relational Ratios

| | EX 1 | EX 2 | EX 3 | EX 4 | EX 5 | EX 6 |
|---|---|---|---|---|---|---|
| Hydrophilic Matrix Comp. (HMC) | 20.5 | 29.0 | 20.0 | 18.6 | 20.5 | 22.4 |
| Total Matrix Mass | 90.0 | 99.0 | 65.0 | 70.8 | 50.0 | 55.0 |
| Ratio Liquid to Semisolid Lipid | 3.7 | 5.5 | 2.4 | 2.6 | 6.3 | 7.0 |
| Ratio of Anionic Pol.:Cationic Pol. | 0.8 | 0.5 | 0.8 | 0.2 | 0.5 | 0.3 |
| Ratio of TLV to HP | 6.8 | 2.8 | 3.4 | 3.8 | 2.5 | 1.8 |
| Ratio of SA to THP | 5.3 | 1.2 | 7.0 | 2.6 | 18.0 | 7.3 |
| Ratio of TLV to HMC | 3.3 | 2.2 | 2.2 | 2.7 | 1.4 | 1.4 |
| Ratio of API to HMC | 0.5 | 0.03 | 1.8 | 1.6 | 2.4 | 2.0 |
| Ratio of API to TLV | 0.1 | 0.02 | 0.8 | 0.6 | 1.7 | 1.4 |
| Ratio API to Total Matrix | 0.1 | 0.01 | 0.5 | 0.4 | 1.0 | 0.8 |

TABLE 15

Exemplary Abuse Deterrent Controlled Release Matrix Compositions

Weight Percentage (%)

| Ingredient | EX 1 | EX 2 | EX 3 | EX 4 | EX 5 | EX 6 |
|---|---|---|---|---|---|---|
| Olive Oil | 42.0 | 60.0 | 31.0 | 36.0 | 25.0 | 35.0 |
| Gelucire ® | 16.0 | 32.0 | 7.0 | 14.0 | 6.0 | 12.0 |
| Poloxamer | 15.0 | 3.5 | 7.0 | 6.0 | 1.0 | 11.0 |
| Polyvinylpyrrolidone | 1.0 | 1.0 | 10.0 | 4.7 | 5.0 | 9.0 |
| Carbopol ® 971 A | 5.0 | 1.0 | 3.0 | 3.1 | 4.0 | 8.0 |
| Meglumine | 4.0 | 0.5 | 2.8 | 2.4 | 3.0 | 8.0 |
| EUDRAGIT ® EPO | 7.0 | 1.0 | 4.3 | 4.6 | 6.0 | 12.0 |
| Active Pharmaceut. Ingredient (API) | 10.0 | 1.0 | 35.0 | 29.2 | 50.0 | 5.0 |
| TOTAL | 100 | 100 | 100 | 100 | 100 | 100 |

TABLE 16

Exemplary Abuse Deterrent Controlled Release Matrix Compositions

Weight Percentage (%)

| Ingredient | EX 1 | EX 2 | EX 3 | EX 4 | EX 5 | EX 6 |
|---|---|---|---|---|---|---|
| Soybean Oil | 53.0 | 55.0 | 31.0 | 36.0 | 25.0 | 28.0 |
| Gelucire ® | 10.0 | 5.0 | 3.0 | 9.0 | 1.0 | 2.0 |
| Bee's wax | 4.5 | 5.0 | 10.0 | 5.0 | 3.0 | 2.0 |
| Polyvinylpyrrolidone | 6.0 | 1.0 | 10.0 | — | 5.0 | — |
| HPMC 4M | 4.0 | 7.0 | 3.0 | 8.0 | — | 8.0 |
| Polyethylene oxide | — | 15.0 | — | 5.0 | 6.5 | 10.0 |
| Carbopol ® 971 A | 4.5 | 2.0 | 3.0 | 1.0 | 3.0 | 1.0 |
| Aerosil ® | 2.0 | 5.0 | 1.0 | 2.2 | 0.5 | 0.6 |
| EUDRAGIT ® EPO | 6.0 | 4.0 | 4.0 | 4.6 | 6.0 | 3.4 |
| Active Pharmaceut. Ingredient (API) | 10.0 | 1.0 | 35.0 | 29.2 | 50.0 | 45.0 |
| TOTAL | 100 | 100 | 100 | 100 | 100 | 100 |

What is claimed is:

1. An abuse deterrent tamper resistant oral pharmaceutical dosage form comprising a soft capsule shell encapsulating a tamper resistant matrix comprising:
   (a) about 45% to about 52% by mass soybean oil;
   (b) about 1.8% to about 4% by mass polyethylene glycol glyceride ester;
   (c) about 1.8% to about 4% by mass bee's wax;
   (d) about 5% to about 15% by mass of a polyethylene oxide having a molecular weight of about 100,000;
   (e) about 0.5% to about 4% by mass carboxypolymethylene;
   (f) about 2% to about 8% by mass dimethylaminoethyl methacrylate copolymer;
   (g) about 0.5% to about 5% by mass fumed silica; and
   (h) about 5% to about 30% by mass tapentadol hydrochloride.

2. An abuse deterrent oral pharmaceutical dosage form comprising a soft capsule shell encapsulating a tamper resistant matrix comprising:
   (a) about 45% to about 52% by mass soybean oil;
   (b) about 1.5% to about 5% by mass polyethylene glycol glyceride ester;
   (c) about 1.8% to about 4% by mass bee's wax;
   (d) about 2% to about 8% by mass polyvinylpyrrolidone 90;
   (e) about 0.5% to about 4% by mass carbomer polymer;
   (f) about 2% to about 8% by mass dimethylaminoethyl methacrylate copolymer;

(g) about 0.5% to about 5% by mass fumed silica; and
(h) about 5% to about 30% by mass tapentadol hydrochloride.

3. The composition of claim 1, wherein the soft capsule shell comprises:
   (a) about 25-50% by mass of at least one film-forming polymer;
   (b) about 15-25% by mass of at least one plasticizer; and
   (c) about 20-40% by mass of a solvent.

4. The composition of claim 2, wherein the soft capsule shell comprises:
   (a) about 25-50% by mass of at least one film-forming polymer;
   (b) about 15-25% by mass of at least one plasticizer; and
   (c) about 20-40% by mass of a solvent.

* * * * *